United States Patent
Xiong et al.

(10) Patent No.: US 10,466,180 B2
(45) Date of Patent: Nov. 5, 2019

(54) ALPHABETICAL METAMATERIAL GATE/SENSOR DEVICE AND ITS USE TO MEASURE MERCURY

(71) Applicant: NANYANG TECHNOLOGICAL UNIVERSITY, Singapore (SG)

(72) Inventors: Qihua Xiong, Singapore (SG); Cuong Cao, Singapore (SG); Jun Zhang, Singapore (SG)

(73) Assignee: Nanyang Technological University, Singapore (SG)

( * ) Notice: Subject to any disclaimer, the term of this patent is extended or adjusted under 35 U.S.C. 154(b) by 442 days.

(21) Appl. No.: 14/896,515

(22) PCT Filed: Jun. 6, 2014

(86) PCT No.: PCT/SG2014/000264
§ 371 (c)(1),
(2) Date: Dec. 7, 2015

(87) PCT Pub. No.: WO2014/200431
PCT Pub. Date: Dec. 18, 2014

(65) Prior Publication Data
US 2016/0131585 A1    May 12, 2016

Related U.S. Application Data

(60) Provisional application No. 61/833,130, filed on Jun. 10, 2013.

(51) Int. Cl.
*G01N 21/65* (2006.01)
*H01L 27/28* (2006.01)
(Continued)

(52) U.S. Cl.
CPC ............ *G01N 21/658* (2013.01); *B82Y 15/00* (2013.01); *G01N 33/20* (2013.01); *H01L 27/28* (2013.01);
(Continued)

(58) Field of Classification Search
CPC ........ B82Y 30/00; B82Y 5/00; G01N 21/658; G01N 21/554; G01N 21/648; G01N 33/20;
(Continued)

(56) References Cited

PUBLICATIONS

Han et al. "Mercury (II) detection by SERS based on a single gold microshell", Chem. Commun., 2010, v. 46, pp. 5587-5589.*
(Continued)

*Primary Examiner* — Arlen Soderquist
(74) *Attorney, Agent, or Firm* — Seed IP Law Group LLP

(57) ABSTRACT

The present invention relates to a logic gate, comprising a metamaterial surface enhanced Raman scattering (MetaSERS) sensor, comprising (a) alphabetical metamaterials in the form of split ring resonators operating in the wavelength range of from 560 to 2200 nm; and (b) a guanine (G) and thymine (T)-rich oligonucleotide that can, upon presence of potassium cations ($K^+$), fold into a G-quadruplex structure, and in presence of $Hg^{2+}$, form a T-$Hg^{2+}$-T hairpin complex that inhibits or disrupts the G-quadruplex structure formed in presence of $K^+$, as well as methods of operating and using such a logic gate.

15 Claims, 9 Drawing Sheets

Specification includes a Sequence Listing.

(51) Int. Cl.
| | |
|---|---|
| H01L 51/00 | (2006.01) |
| B82Y 15/00 | (2011.01) |
| G01N 33/20 | (2019.01) |
| G01N 33/02 | (2006.01) |
| G01N 33/483 | (2006.01) |

(52) U.S. Cl.
CPC .......... *H01L 51/0093* (2013.01); *G01N 33/02* (2013.01); *G01N 33/483* (2013.01)

(58) Field of Classification Search
CPC ........... G01N 33/5308; G01N 15/0656; G01N 21/255; G01N 21/553; G01N 33/02; G01N 33/483; G02B 1/002; G02B 6/1226; G02B 6/12
USPC ......................................................... 436/74
See application file for complete search history.

(56) References Cited

PUBLICATIONS

Clark, PhD Thesis, "Nanophotonic split-ring resonators as dichroics for molecular spectroscopy", Univ. of Glasgow, 2009, 1-143, file:///C:/Users/ygakh/Documents/e-Red%20Folder/14896515/2009Clarkphd.pdf.*
Breuzard, G. et al, Analytical CHemistry 2003, 75, 4305-4311.*
Wu, W. et al, Applied Physics Letters 2007, 90, paper 063107, 3 pages.*
Tretyakov, S., Metamaterials 2007, 1, 40-43.*
Sheridan, A. K. et al, Applied Physics Letters 2007, 90, paper 143105, 3 pages.*
Aydin, K. et al, New Journal of Physics 2007, 9, paper 326, 11 pages.*
Li, K. et al, Nanotechnology 2008, 19, paper 145306, 7 pages.*
Verellen, N. et al, Nano Letters 2009, 9, 1663-1667.*
Ochsenkuhn, M. A. et al, Chemical Communications 2010, 46, 2799-2801.*
Pryce, I. M. et al, Nano Letters 2010, 10, 4222-4227.*
Liu, S.-D. et al, Journal of Physical Chemistry C 2011, 115, 24469-24477.*
Tseng, M. L. et al, ACSNano 2012, 6, 5190-5197.*
Pelossof,, G. et al, Analytical Chemistry 2012, 84, 3703-3709.*
Yue, W. et al, Journal of Micromechanics and Microengineering 2012, 22, paper 125007, 9 pages.*
Chen, H. et al, Physical Review E 2005, 70, paper 057605, 4 pages.*
Chen, X. et al, Angewandte Chemie International Edition 2006, 45, 1759-1762.*
Lee, J.-S. et al, Angewandte Chemie International Edition 2007, 46, 4093-4096.*
Toth-Fejel, T. T., IEEE Sensors Journal 2008, 8, 1036-1040.*
Wang, Z. et al, Advanced Materials 2008, 20, 3263-3267.*
Liu, N. et al, Advanced Materials 2008, 20, 4521-4525.*
Lahiri, B. et al, Optics Express 2009, 17, 1107-1115.*
Cubukcu, E. et al, Applied Physics Letters 2009, 95, paper 043113, 3 pages.*
Valev, V. K. et al, Nano Letters 2009, 9, 3945-3948.*
Hu, W. Q. et al, Optics Express 2009, 17, 20843-21849.*
Chang, Y.-T. et al, Optics Express 2010, 18, 9561-9569.*
Lassiter, J. B. et al, Nano Letters, 2010, 10, 3184-3189.*
Pors, A. et al, Journal of the Optical Society of America 2010, 27, 1680-1687.*
Clark, A. W. et al, Small 2011, 7, 119-125.*
Verellen, N. et al, Nano Letters 2011, 11, 391-397.*
Zhang, X.-B. et al, Annual Review of Analytical Chemistry 2011, 4, 105-128.*
Chen, J. et al, Optics Express 2011, 19, 5970-5978.*
Jiang, Z. H. et al, ACS Nano 2011, 5, 4641-4647.*
Pryce, I. M. et al, ACS Nano 2011, 5, 8167-8174.*
Liu, J.-T. et al, Journal of Physics D: Applied Physics 2013, 46, paper 195104, 6 pages.*
Adato et al., "Ultra-sensitive vibrational spectroscopy of protein monolayers with plasmonic nanoantenna arrays," *PNAS* 106(46):19227-19232 (Nov. 17, 2009).
Adleman, "Molecular Computation of Solutions to Combinatorial Problems," *Science, New Series* 266(5187):1021-1024 (Nov. 11, 1994).
Alvarez-Puebla et al., "Surface-enhanced Raman scattering for ultrasensitive chemical analysis of 1 and 2-naphthalenethiols," *Analyst* 129:1251-1256 (2004).
Anker et al., "Biosensing with plasmonic nanosensors," *Nature Materials* 7:442-453 (Jun. 2008).
Bates et al., "Discovery and development of the G-rich oligonucleotide AS1411 as a novel treatment for cancer," *Experimental and Molecular Pathology* 86:151-164 (2009).
Bi et al., "Colorimetric Logic Gates Based on Supramolecular DNAzyme Structures," *Angew. Chem.* 122:4540-4544 (2010).
Cao et al., "Metamaterials-Based Label-Free Nanosensor for Conformation and Affinity Biosensing,"*ACSNano*, Published online, www.acsnano.org, 10.1021/nn401645t (Aug. 17, 2013).
Clark et al., "Plasmonic Split-Ring Resonators as Dichroic Nanophotonic DNA Biosensors," *J. Am. Chem. Soc.* 131:17615-17619 (2009).
Clarkson, "The Toxicology of Mercury and Its Chemical Compounds," *Critical Reviews in Toxicology* 36:609-662 (2006).
Clarkson et al., "The Toxicology of Mercury—Current Exposures and Clinical Manifestations," *New England Journal of Medicine* 349(18):1731-1737 (Oct. 30, 2003).
Clever et al., "The Solubility of Mercury and Some Sparingly Soluble Mercury Salts in Water and Aqueous Electrolyte Solutions," *J. Phys. Chem. Ref. Data* 14(3):631-680 (1985).
Corrigan et al., "Optical plasmonic resonances in split-ring resonator structures: an improved LC model," *Optics Express* 16(24) (15 pages) (Nov. 24, 2008).
De Silva et al., "Molecular logic and computing," *Nature Nanotechnology* 2:399-410 (Jul. 2007).
Dodson et al., "Optimizing Electromagnetic Hotspots in Plasmonic Bowtie Nanoantennae," *The Journal of Physical Chemistry Letters* 4:496-501 (2013).
Draine et al., "Discrete-dipole approximation for scattering calculations," *J. Opt. Soc. Am. A* 11(4):1491-1499 (Apr. 1994).
Draine, "The Discrete-Dipole Approximation and Its Application to Interstellar Graphite Grains," *The Astrophysical Journal* 333:848-872 (Oct. 15, 1988).
Elbaz et al., "DNA computing circuits using libraries of DNAzyme subunits," *Nature Nanotechnology* 5:417-422 (Jun. 2010).
Enkrich et al., "Magnetic Metamaterials at Telecommunication and Visible Frequencies," *Physical Review Letters* PRL 95, 203901 (4 pages) (2005).
Freeman et al., "Multiplexed Analysis of $Hg^{2+}$ and $Ag^+$ Ions by Nucleic Acid Functionalized CdSe/ZnS Quantum Dots and Their Use for Logic Gate Operations," *Angew. Chem. Int. Ed.* 48:7818-7821 (2009).
Hatab et al., "Free-Standing Optical Gold Bowtie Nanoantenna with Variable Gap Size for Enhanced Raman Spectroscopy," *Nano Letters* 10:4952-4955 (2010).
Huang et al., "A reversible fluorescence nanoswitch based on bifunctional reduced graphene oxide: use for detection of $Hg^{2+}$ and molecular logic gate operation," *Chem. Comm.* 47:7800-7802 (2011).
Jiang et al., "Highly-Efficient Gating of Solid-State Nanochannels by DNA Supersandwich Structure Containing ATP Aptamers: A Nanofluidic IMPLICATION Logic Device," *Journal of the American Chemical Society* 134:15395-15401 (2012).
Kabashin et al., "Plasmonic nanorod metamaterials for biosensing," *Nature Materials* 8:867-871 (Nov. 2009).
Lee et al., "Colorimetric Detection of Mercuric Ion ($Hg^{2+}$) in Aqueous Media using DNA-Functionalized Nanoparticles," *Angew. Chem.* 119:4171-4174 (2007).
Li et al., "Label-Free Colorimetric Detection of Aqueous Mercury Ion ($Hg^{2+}$) Using $Hg^{2+}$-Modulated G-Quadruplex-Based DNAzymes," *Analytical Chemistry* 81(6):2144-2149 (Mar. 15, 2009).

(56) References Cited

PUBLICATIONS

Li et al., "Optical Analysis of $Hg^{2+}$ Ions by Oligonucleotide-Gold-Nanoparticle Hybrids and DNA-Based Machines," *Angew. Chem.* 120:3991-3995 (2008).

Li et al., "Shell-isolated nanoparticle-enhanced Raman spectroscopy," *Nature Letters* 464:392-395 (Mar. 18, 2010).

Li et al., "Potassium-Lead-Switched G-Quadruplexes: A New Class of DNA Logic Gates," *J. Am. Chem. Soc.* 131:15082-15083 (2009).

Linden et al., "Magnetic Response of Metamaterials at 100 Terahertz," *Science* 306:1351-1353 (Nov. 19, 2004).

Liu et al., "Coupling Effects in Optical Metamaterials," *Angew. Chem. Int. Ed.* 49:9838-9852 (2010).

Liu et al., "Nanoantenna-enhanced gas sensing in a single tailored nanofocus," *Nature Materials* 10:631-636 (Aug. 2011).

Liu et al., "Multiplexed Aptasensors and Amplified DNA Sensors Using Functionalized Graphene Oxide: Application for Logic Gate Operations," *ACSNano* 6(4):3553-3563 (2012).

Morel et al., "The Chemical Cycle and Bioaccumulation of Mercury," *Annu. Rev. Ecol. Syst.* 29:543-566 (1998).

Miura et al., "Structural Polymorphism of Telomere DNA: Interquadruplex and Duplex-Quadruplex Conversions Probed by Raman Spectroscopy," *Biochemistry* 33:7848-7856 (1994).

Nie et al., "Probing Single Molecules and Single Nanoparticles by Surface-Enhanced Raman Scattering," *Science* 275:1102-1106 (Feb. 21, 1997).

Nikolaenko et al., "Carbon Nanotubes in a Photonic Metamaterial," *Physical Review Letters* PRL 104, 153902 (4 pages) (2010).

Park et al., "Simple and Universal Platform for Logic Gate Operations Based on Molecular Beacon Probes," *Small* 8(14):2203-2212 (2012).

Pelossof et al., "Amplified Surface Plasmon Resonance Based DNA Biosensors, Aptasensors, and $Hg^{2+}$ Sensors Using Hemin/G-Quadruplexes and Au Nanoparticles," *Chem. Eur. J.* 17:8904-8912 (2011).

Rodriguez-Lorenzo et al., "Plasmonic nanosensors with inverse sensitivity by means of enzyme-guided crystal growth," *Nature Materials* 11:604-607 (Jul. 2012).

Rusciano et al., "Label-Free Probing of G-Quadruplex Formation by Surface-Enhanced Raman Scattering," *Analytical Chemistry* 83:6849-6855 (2011).

Schuller et al., "Plasmonics for extreme light concentration and manipulation," *Nature Materials* 9:193-204 (Mar. 2010).

Shelby et al., "Experimental Verification of a Negative Index of Refraction," *Science* 292:77-79 (Apr. 6, 2001).

Stobiecka et al., "Mercury/Homocysteine Ligation-Induced ON/OFF-Switching of a T-T Mismatch-Based Oligonucleotide Molecular Beacon," *Analytical Chemistry* 84:4970-4978) (2012).

Wang et al., "Graphene-Based Aptamer Logic Gates and Their Application to Multiplex Detection," *ACSNano* 6(8):6659-6666 (2012).

Wilcox et al., "Method of Measuring Oligonucleotide-Metal Affinities: Interactions of the Thrombin Binding Aptamer with $K^+$ and $Sr^{2+}$," *Analytical Chemistry* 80(7):2365-2371 (2008).

Willner et al., "DNAzymes for sensing, nanobiotechnology and logic gate applications," *Chem. Soc. Rev.*, 37:1153-1165 (2008).

Witlicki et al., "Molecular Logic Gates Using Surface-Enhanced Raman-Scattered Light," *J. Am. Chem. Soc.* 133:7288-7291 (2011).

Wu et al., "Fano-resonant asymmetric metamaterials for ultrasensitive spectroscopy and identification of molecular monolayers," *Nature Materials* 11:69-75 (Jan. 2012).

Xu et al., "Flexible Visible-Infrared Metamaterials and Their Applications in Highly Sensitive Chemical and Biological Sensing," *Nano Letters* 11:3232-3238 (2011).

Ye et al., "Highly Sensitive Detection of Mercury (II) Ions by Fluorescence Polarization Enhanced by Gold Nanoparticles," *Angew. Chem. Int. Ed.* 47:8386-8389 (2008).

Zhou et al., "Turnable subradiant lattice plasmons by out-of-plane dipolar interactions," *Nature Nanotechnology* 6:423-427 (Jul. 2011).

\* cited by examiner

| U | (nm) |
|---|---|
| a | 160 |
| b | 80 |
| w | 80 |
| sx | 320 |
| sy | 320 |
| dx | 160 |
| dy | 160 |

| Y | (nm) |
|---|---|
| a | 160 |
| b | 80 |
| w | 80 |
| sx | 320 |
| sy | 320 |
| dx | 160 |
| dy | 160 |

| S | (nm) |
|---|---|
| a | 160 |
| b | 80 |
| w | 80 |
| sx | 320 |
| sy | 320 |
| dx | 160 |
| dy | 160 |

| H | (nm) |
|---|---|
| a | 160 |
| b | 80 |
| w | 80 |
| sx | 320 |
| sy | 320 |
| dx | 160 |
| dy | 160 |

| Ubar | (nm) |
|---|---|
| a | 160 |
| b | 128 |
| w | 80 |
| sx | 320 |
| sy | 320 |
| dx | 240 |
| dy | 96 |
| d | 96 |

| V | (nm) |
|---|---|
| a | 160 |
| w | 80 |
| sx | 320 |
| sy | 320 |
| dx | 160 |
| dy | 160 |

| Pattern | h (1mm) | $P_x$(785nm, 1380 cm$^{-1}$) | | | $P_y$(785nm, 1380 cm$^{-1}$) | | |
|---|---|---|---|---|---|---|---|
| | | $I_{sers}/I_{bulk}$ | $R_{lattice}$ | EF(10$^7$) | $I_{sers}/I_{bulk}$ | $R_{lattice}$ | EF(10$^7$) |
| S30 | 1 | 7.08 | 0.53 | 2.48 | 12.92 | 0.53 | 4.53 |
| S40 | 1 | 1.88 | 0.53 | 0.66 | 20.89 | 0.32 | 12.14 |
| S50 | 1 | 3.10 | 0.53 | 1.09 | 3.05 | 0.53 | 1.07 |
| H30 | 1 | 9.28 | 0.53 | 3.26 | 4.51 | 0.53 | 1.58 |
| H40 | 1 | 10.31 | 0.53 | 3.62 | 19.21 | 0.53 | 6.76 |
| H50 | 1 | 8.06 | 0.53 | 2.83 | 2.60 | 0.53 | 0.91 |
| V30 | 1 | 3.32 | 0.32 | 1.93 | 18.7 | 0.32 | 10.56 |
| V40 | 1 | 2.64 | 0.32 | 1.53 | 3.38 | 0.53 | 1.19 |
| V50 | 1 | 4.11 | 0.32 | 2.39 | 4.45 | 0.53 | 1.56 |
| Y30 | 1 | 12.37 | 0.32 | 7.19 | 0.37 | 0.53 | 0.13 |
| Y40 | 1 | 4.14 | 0.53 | 1.45 | 14.02 | 0.53 | 4.92 |
| Y50 | 1 | 5.61 | 0.53 | 1.97 | 5.87 | 0.53 | 2.06 |

SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: GT-rich oligonucleotide

<400> SEQUENCE: 1
ggtggtggtg gttgtggtgg tggtgg      26

ALPHABETICAL METAMATERIAL GATE/SENSOR DEVICE AND ITS USE TO MEASURE MERCURY

CROSS-REFERENCE TO RELATED APPLICATIONS

This application makes reference to and claims the benefit of priority of an application for "Tailoring Plasmonic Metamaterials for High Fidelity Molecular Logic and Ultrasensitive Sensing" filed on Jun. 10, 2013, with the United States Patent and Trademark Office, and there duly assigned Ser. No. 61/833,130. The content of said application filed on Jun. 10, 2013, is incorporated herein by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_503USPC SEQUENCE LISTING.txt. The text file is 543 bytes, was created on Dec. 6, 2015, and is being submitted electronically via EFS-Web.

TECHNICAL FIELD OF THE INVENTION

The invention relates to a DNA logic gate based on a metamaterial SERS sensor and methods of operating and using such a logic gate.

BACKGROUND OF THE INVENTION

Since, the first introduction by Adleman in 1994 (Adleman, Science 266, 1021-1024 (1994)), DNA logic gates have been considered as the future of computation technology where their small size is a distinct advantage over the conventional top-down semiconductor technology. They also exhibit important applications in life sciences as smart sensing and diagnostic platforms owing to the unique properties of DNA such as self-assembly, specific recognition and conformation modulation upon exposing to external stimuli (i.e. metallic ions, proteins) (Elbaz, J., et al. Nat. Nanotechnol. 5, 417-422 (2010)). Along this line, DNA-based systems (e.g. DNAzymes (Bi, S., Yan, Y., Hao, S. & Zhang, S. Angew. Chem. Int. Ed. 49, 4438-4442 (2010)) molecular beacons (Park, K. S., Seo, M. W., Jung, C., Lee, J. Y. & Park, H. G. Small 8, 2203-2212 (2012)), guanine-rich oligonucleotides (G-quadruplexes) (Li, T., Wang, E. & Dong, S. J. Am. Chem. Soc. 131, 15082 (2009)), aptamers (Liu, X., Aizen, R., Freeman, R., Yehezkeli, O. & Willner, I. ACS Nano 6, 3553-3563 (2012)) have been devised on different nanometer scale carriers such as graphene and graphene oxide (Wang, L., et al. ACS Nano 6, 6659-6666 (2012)), solid-state nanochannels (Jiang, Y., Liu, N., Guo, W., Xia, F. & Jiang, L. J. Am. Chem. Soc. 134, 15395-15401 (2012)), quantum dots (Freeman, R., Finder, T. & Willner, I. Angew. Chem. Int. Ed. 48, 7818-7821 (2009)), and gold nanodisc arrays (Witlicki, E. H., et al. J. Am. Chem. Soc. 133, 7288-7291 (2011)) for various logic gate operations and biosensing applications. Those DNA logic operations mostly rely on fluorescence and enzyme cascades to generate "ON" or "OFF" output signals which involve complex handling and analysis procedures, thus restricting the performance and applications of the sophisticated logic devices.

In addition, it still remains very challenging to realize a label-free and switchable DNA logic gate-based biosensing platform that can selectively respond to extremely low concentration of the chemical and biological stimuli.

There is a recent emergence of plasmonic metamaterials capable of providing high electromagnetic enhancement (hot-spots) for surface enhanced Raman scattering (SERS) (hereafter called MetaSERS) (Xu, X., et al. Nano Lett. 11, 3232-3238 (2011)). The most prevailing SERS sensors are based upon chemically synthesized colloidal nanoparticles (Nie, S. & Emery, S. Science 275, 1102-1106 (1997)), but they have the disadvantage of poor reproducibility. Recent advances have employed a variety of top-down fabrication techniques which enable large-scale and reproducible patterns for SERS substrates ranging from bow-tie nanoantennae (Hatab, N. A., et al. Nano Lett. 10, 4952-4955 (2010)) to asymmetric Fano resonance structures (Zhou, W. & Odom, T. W. Nat. Nanotechnol. 6, 423-427 (2011)). In contrast to these structures, plasmonic metamaterials have recently been demonstrated to offer effective ways to tailor the concentration of light to form desired hot-spots by controlling the size and shape of plasmonic structures (Schuller, J. A., et al. Nat. Mater. 9, 193-204 (2010)). By properly designing the micro- or nano-scaled metallic sub-wavelength structures, e.g. "split ring resonators (SRRs)", one can tune the operating frequency of metamaterials from microwave (Shelby, R., Smith, D. & Schultz, S. Science 292, 77-79 (2001)) to visible regime (Xu, X., et al. (2011)). However, most of metamaterial-based biosensing focuses on the localized surface plasmon resonance (LSPR) shifts induced by absorbed molecules (Liu, N., Tang, M. L., Hentschel, M., Giessen, H. & Alivisatos, A. P. Nat. Mater. 10, 631-636 (2011)), in which the shift depends on the effective refractive index of the target molecules thus exhibiting no chemical fingerprints. Recently, Fano-resonant asymmetric metamaterials have been introduced to demonstrate the ultrasensitive sensing and identification of molecular monolayers by tuning the resonant peak towards (away from) protein's vibrational fingerprint and monitoring the infrared reflectance spectra (Wu, C., et al. Nat. Mater. 11, 69-75 (2012)).

Structural and functional information encoded in DNA combined with unique properties of nanomaterials could be of use for the construction of novel biocomputational circuits and intelligent biomedical nanodevices. However, at present their practical applications are still limited by either low reproducibility of fabrication, modest sensitivity, or complicated handling procedures.

Bivalent mercury ions $Hg^{2+}$ are the most stable inorganic forms of mercury contaminant in environment and food products and are responsible for a number of life-long fatal effects in human health such as kidney damage, brain damage, and other chronic diseases (Clarkson, T. W. & Magos, L. Crit. Rev. Toxicol. 36, 609-662 (2006)). According to the United States Environmental Protection Agency (EPA), the maximum amount of mercury should be lower than ppb and ppm levels for drinking water and food products, respectively (Clarkson, T. W. & Magos, L. (2006)). However, because mercury has a strong bioaccumulation effect through the food chain (Morel et al. Annu. Rev. Ecol. Syst. 29, 543-566 (1998)), there exists a great demand and also a significant challenge for development of a method that allows facilely monitoring the concentration of mercury below the defined exposure limit level.

SUMMARY OF THE INVENTION

The present invention meets some of the above needs and overcomes some of the known drawbacks of existing technologies by providing, in a first aspect of the invention, a logic gate, comprising a metamaterial surface enhanced Raman scattering (MetaSERS) sensor, comprising alphabetical metamaterials in the form of split ring resonators operating in the wavelength range of from 560 nm to 2200 nm; and a guanine (G) and thymine (T)-rich oligonucleotide that can, upon presence of potassium cations ($K^+$), fold into a G-quadruplex structure, and in presence of $Hg^{2+}$, form a T-$Hg^{2+}$-T hairpin complex that inhibits or disrupts the G-quadruplex structure formed in presence of $K^+$. Such a logic gate can, depending on the presence of potassium, mercury and/or iodide ions switch between three states and thus form an "AND", "OR" or "INHIBIT" logic gate.

Another aspect of the invention relates to a method of operating the logic gate described herein, comprising (a) providing the MetaSERS sensor as described above, wherein the oligonucleotide is comprised in an aqueous solution, wherein the solution is in contact with the split ring resonators, preferably the split ring resonators are immersed in the solution; (b) (i) adding potassium ions ($K^+$) and/or (ii) adding mercury ions ($Hg^{2+}$) and/or (iii) adding iodide ions ($I^-$), wherein steps (i), (ii) and (iii) are performed individually or simultaneously and in any order to generate an AND, OR or INHIBIT logic operation; and (c) measuring the SERS signal.

A further aspect of the invention relates to a method for the detection of mercury ions ($Hg^{2+}$) in a sample, comprising (a) providing a MetaSERS sensor, comprising alphabetical metamaterials in the form of split ring resonators operating in the wavelength range from 560 nm to 2200 nm; and an aqueous solution comprising a guanine (G) and thymine (T)-rich oligonucleotide, wherein in the presence of the potassium cations ($K^+$) the oligonucleotide adopts a G-quadruplex structure, and in presence of $Hg^{2+}$, forms a T-$Hg^{2+}$-T hairpin complex that inhibits or disrupts the G-quadruplex structure, wherein the solution is in contact with the split ring resonators, preferably the split ring resonators are immersed in the solution; (b) contacting the MetaSERS sensor with the sample in the presence of potassium ions ($K^+$) under conditions that allow any $Hg^{2+}$ that is present in the sample to form a T-$Hg^{2+}$-T hairpin complex with the oligonucleotide that inhibits formation of or disrupts the G-quadruplex structure; and (c) measuring the SERS signal.

A further aspect of the invention relates to a device comprising the logic gate as described herein.

A further aspect of the invention relates to use of a logic gate as described herein.

A further aspect of the invention relates to use of a logic gate as described herein for mercury ion ($Hg^{2+}$) detection in a sample.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
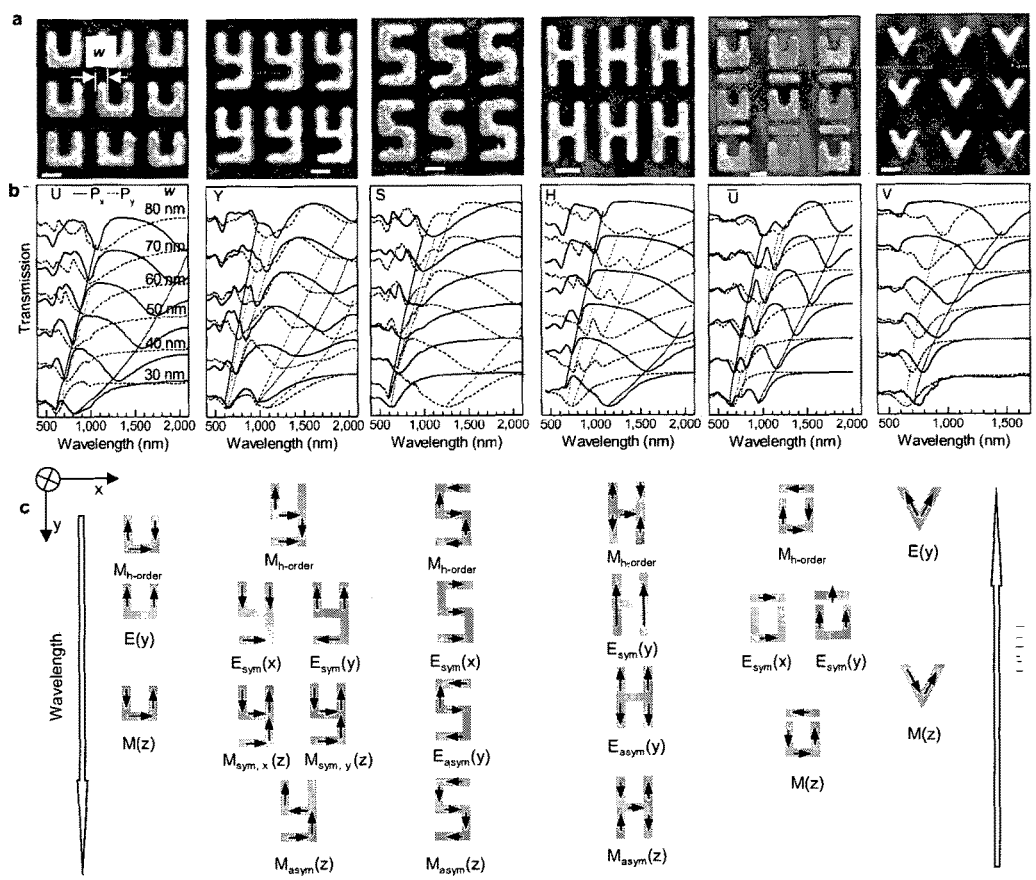
FIG. 1. SEM images, transmission spectra and schematic diagrams of the plasmon hybridization. a, A typical SEM images of U, Y, S, H, U-bar and V shaped gold metamaterials with w=40 nm fabricated on a flexible PEN or ITO/Glass substrate. b, Transmission spectra of SRRs with different widths of w=80-30 nm for U, Y, S, H, U-bar and V shapes. The solid curves correspond to the $P_x$ polarization, while the dashed curves correspond to the $P_y$ polarization. The color lines highlight the trends of resonance depending on the size of unit. c, Dipole current distribution of the plasmon hybridization modes for different shapes. For each shape, the modes are arranged by the order of wavelength (energy), with two degenerate cased for Y and U-bar shapes. The corresponding simulated results can be found in FIG. 10.

A first aspect of the invention relates to a logic gate, comprising a metamaterial surface enhanced Raman scattering (MetaSERS) sensor, comprising (a) alphabetical metamaterials in the form of split ring resonators operating in the wavelength range of from 560 nm to 2200 nm; and (b) a guanine (G) and thymine (T)-rich oligonucleotide that can, in presence of potassium cations ($K^+$), fold into a G-quadruplex structure, and in presence of $Hg^{2+}$, form a T-$Hg^{2+}$-T hairpin complex that inhibits or disrupts the G-quadruplex structure formed in presence of $K^+$.

As used herein a "logic gate" may be a physical device implementing a Boolean function; that is, it performs a logical operation on one or more logical inputs, and produces a single logical output. With amplification, logic gates can be cascaded in the same way that Boolean functions can be composed, allowing the construction of a physical model of all of Boolean logic, and therefore, all of the algorithms and mathematics that can be described with Boolean logic.

As used herein, the term "metamaterial" refers generally to an artificial material that is engineered to exhibit and/or to provide electromagnetic behavior that is not found in a natural material. For example, metamaterials may be designed to provide electric or magnetic resonances where there are no equivalent materials in nature. This may be carried out by patterning one or more elements that are comprised in a metamaterial in one or more dimensions, with each element having physical dimensions less than or on the order of an incident wavelength in the direction of wave propagation. In so doing, each of the elements comprised in the metamaterial may be patterned to exhibit specific electric and magnetic polarizations in response to an applied electromagnetic field.

Examples of metamaterial include, but are not limited to, lattices formed from straight wire conductors and arrays of split-ring resonators, both of which may be fabricated on a suitable substrate. The term "resonator", as used herein, refers to a structure having, or capable of having, a desired resonant frequency. The metamaterials used in accordance with the present invention are alphabetical metamaterials in the form of split ring resonators.

In general terms, a split-ring resonator refers to a type of resonator, comprising a conductive shape such as a ring that is broken in at least one location on the shape by a non-conductive gap of air or other dielectric material. When the split-ring resonator is placed in an electro-magnetic field, fluctuation of the electro-magnetic field causes a circular electric current to be induced in the conductive shape, which in turn results in charge accumulation across the gap(s) in the shape. The electric field that builds due to the charge at the gap counteracts the circular current, leading to storage of substantial amounts of energy in the vicinity of the gaps. In addition, magnetic field energy is concentrated in the region enclosed by the shape. Accordingly, a split ring resonator may be considered as a resonator that reacts to a perpendicular magnetic field, and may be characterized by the effective capacitance of the gaps and effective inductance of the loop defined by the shape. As described herein the shape is alphabetical (thus alphabetical metamaterials). The split ring resonators are tunable with respect to their operating range by varying their shape morphologies and/or bar width. In various embodiments the alphabetical split ring resonators are U, V, H, S Ū, C, W, Z, E, I, M or Y-shaped and have a bar widths from about 30 nm to about 80 nm, preferably a bar width from 30 to 50 nm, more preferably 30 to 40 nm.

In various embodiments, the alphabetical split ring resonators which are composed from a basic shape of "U" or "V" may be used. For example, the split-ring resonator may be formed from a single "U" arranged in any orientation, such as C-shaped, reverse C-shaped (i.e. mirror image of a C-shaped), U-shaped, reverse U-shaped (i.e. mirror image of a U-shaped, or n-shaped), or a U shape oriented at any angle to the vertical axis. As another example, the split-ring resonator may be formed from a single "V" arranged in any orientation, such as V-shaped, reverse V-shaped, >-shaped, <-shaped, or a V shape oriented at any angle to the vertical axis. The split-ring resonator may also be formed from a plurality of "U", "V", or their combination. For example, the split-ring resonator may be formed from two "U" and/or two "V" arranged in any orientation, such as E-shaped, H-shaped, I-shaped, M-shaped, S-shaped, W-shaped, Y-shaped, Z-shaped, or their reverse. In various embodiments, the split-ring resonators are C-shaped, E-shaped, H-shaped, S-shaped, U-shaped, U-bar shaped (i.e. "Ū"), V-shaped, W-shaped or Y-shaped. Each of the two "U" and/or "V" may be of the same size or a different size. For example, where two "U" are arranged to form an S-shaped resonator, the top portion of the S-shaped resonator (the first "U") may be smaller than the bottom portion of the S-shaped resonator (the second "U"). Accordingly, the least line width w of each "U" or "V" that is used to form the S-shaped resonator may be the same or different. When they are combined and arranged to form a single shape "S", the least line width of the S-shaped resonator corresponds to the smallest dimension on the periphery of the split-ring resonator, which may be the smaller w of each of the two "U" or "V". As discussed herein, although the split-ring resonators are generally formed from two "U" and/or "two "V", the split-ring resonator may also be formed from three, four or five "U" and/or "V" arranged in any orientation, so long as the least line width of the formed shape is from about 30 to about 50 nm, preferably about 30 nm to about 40 nm thereby rendering it operable in the wavelength range of from 560 nm to 2200 nm.

In various embodiments the patterns are U, V, H, S and/or Y shaped metamaterials with bar-width from 30 to 50 nm. The alphabetical metamaterials may be functionalized with a layer of 2-naphthenethiol molecules. In various embodiments at a given laser wavelength, for instance 785 nm the U shape has a width of 40. In various embodiments at a given laser wavelength, for instance 785 nm the V shape has a width of 30. In various embodiments at a given laser wavelength, for instance 785 nm the H shape has a width of 40. In various embodiments at a given laser wavelength, for instance 785 nm the S shape has a width of 40. In various embodiments at a given laser wavelength, for instance 785 nm the Y shape has a width of 30

In various embodiments the logic gate MetaSERS sensor comprises a suitable substrate on which the alphabetic metamaterials in the form of split ring resonators are formed. A suitable substrate may include rigid substrates such as silicon or quartz, or flexible substrates such as a polymer.

To form the resonators on the substrate, a layer of a noble metal is deposited on the patterned substrate. The noble metal may be deposited by any suitable methods, such as thermal evaporation or electron beam evaporation. Examples of a noble metal include silver (Ag), palladium (Pd), gold (Au), platinum (Pt), iridium (Ir), osmium (Os), rhodium (Rh) and ruthenium (Ru). In various embodiments, the noble metal comprises gold, silver, or alloys thereof. In one embodiment, the noble metal consists substantially of gold. The thickness of the noble metal layer may range from about 5 nm to about 500 nm on the surface of the patterned substrate, such as about 5 nm to about 200 nm, about 5 nm to about 100 nm, about 5 nm to about 50 nm, about 5 nm to about 20 nm, or about 30 nm. In various embodiments the split ring resonators comprise a gold (Au) film, preferably of a thickness of 10 to 50 nm, deposited on the surface.

The term "wavelength range" as used herein, relates to electromagnetic waves. The sensor described herein operates in the wavelength range of from 560 nm to 2200 nm. In various embodiments the sensor may operate at a wavelength that is greater than about 700 nm up to about 1 mm In various embodiments the sensor may operate at wavelengths of about 700 to about 1400 nm, preferably 750-1400 nm. The term "about", as used herein, in relation to numerical values means said reference numerical value ±10%, preferably ±5%.

The term "oligonucleotide" as used herein refers to any nucleic acid molecule comprising more than 2 nucleotides that has the above described properties, i.e. can in principle form a G-quadruplex and a T-$Hg^{2+}$-T hairpin loop. Preferably, the oligonucleotide has a length of up to 50 nucleotides, more preferably 24 to 30 nucleotides. Oligonucleotides include for instance DNA molecules, RNA molecules and analogues of DNA or RNA comprising modifications in the backbones, internucleotide linkages, sugars or bases. The sequence of the oligonucleotide may be derived from a natural template or may be artificially designed. Preferably, the oligonucleotide is DNA. In various embodiments, the oligonucleotide is a single-stranded oligonucleotide, preferably single-stranded DNA (ssDNA). The oligonucleotides are preferably synthetic constructs. Methods for generating an oligonucleotide of a desired sequence are well-known in the art and numerous commercial suppliers are active in this field.

The feature that the oligonucleotide can, in presence of potassium cations ($K^+$), fold into a G-quadruplex structure, and in presence of $Hg^{2+}$, form a T-$Hg^{2+}$-T hairpin complex that inhibits or disrupts the G-quadruplex structure formed in presence of $K^+$, refers to the general capability of the oligonucleotide to adopt such a conformation. This capability is dependent on the sequence of the oligonucleotide, with the concrete sequence requirements, for example G-rich for G-quadruplex formation, and T-rich for T-mercury-T hairpin formation, being known to those skilled in the art. "G-rich", as used herein, means that the oligonucleotide comprises at least 4 guanine bases, preferably 4 sequence stretches that each comprises 1 or more, preferably at least 2 or 3 guanine bases. "T-rich", as used herein, similarly means that the oligonucleotide comprises two or more thymine bases, preferably one or more sequence stretches wherein two or more thymine bases are directly adjacent to each other or separated by no more than 6 nucleotides. Further, the capability of the oligonucleotide to adopt such a structure is of course dependent on the environment. Typically, the environment is an aqueous solution, that may be buffered and have a physiological pH of about 7.4, at standard conditions, i.e. a temperature of about 20° C. and a pressure of 1013 mbar. The feature is thus to be understood that the oligonucleotide can adopt such a conformation under the given conditions. "In presence of", as used in relation to the ions that influence the conformation of the oligonucleotide, i.e. the potassium, mercury and iodide ions, means that the concentration of the respective ion species is high enough to allow the oligonucleotide to adopt the desired conformation. For example, to adopt the G-quadruplex structure, the concentration of potassium ions has to be high enough to allow complex formation. Similarly, for being able to disrupt the G-quadruplex structure or prevent its formation and at the same time allow formation of a T-$Hg^{2+}$-T hairpin, the $Hg^{2+}$ concentration has to be high enough, for example in absolute amounts as well as in relative amounts compared to $K^+$ ions that may be present. The necessary concentrations are however known to those skilled in the art or can be readily determined by using routine experimentation, such as the techniques described herein.

Various nucleotide analogues are known and can be incorporated as part of, or replaced in its entirety, the oligonucleotide of the present invention. A nucleotide analogue as defined herein is a nucleotide modified at the backbone, internucleotide linkage, sugar or base moiety.

Modifications at the backbone or internucleotide linkage moiety include peptide nucleic acid (PNA) and substitution of the phosphate group by phosphorothioate. Modifications at the sugar moiety include locked nucleic acid (LNA) and substitution of the 2'-OH group. Modifications at the base moiety include alterations to A, T/U, G and C, as well as various purine/pyrimidine or non-purine/pyrimidine bases. Modifications of these different moieties can be applied on the same nucleotide in concert. Incorporation of nucleotide analogues within the oligonucleotide can influence the stability of the conformations the oligonucleotide can adopt, i.e. also the ease of switching between different states, or the general stability of the oligonucleotide, for example towards hydrolysis.

As used herein, the term "G-quadruplex" refers to a four-stranded helical nucleic acid structure comprising multiple stacked G-tetrads, each of which consists of four guanine bases that associate in a cyclical manner through Hoogsteen hydrogen bonds and are further stabilized through coordination to a cation in the center. Coordinating cations may include alkali metal cations such as potassium cations ($K^+$). For formation of such a G-quadruplex structure, it is typically required that the oligonucleotide comprises at least four guanine-rich sequence stretches.

As used herein, the term $T-Hg^{2+}-T$ hairpin, relates to a secondary structure, wherein two thymine bases are complexed with a mercury (II) ion such that the nucleic acid strand forms a hairpin structure.

In various embodiments, the G- and T-rich oligonucleotide has the consensus nucleotide sequence $(((G)_x(T)_y)_m(X)_n((T)_y(G)_x)_o)_p$, wherein X is A, T, G or C, each x is independently an integer from 1 to 4, preferably 2 to 3, each y is independently 1 or 2, preferably 1, each m is independently an integer from 1 to 10, preferably 3 to 5, each n is independently 0 or an integer from 1 to 10, preferably 1 to 4, each o is independently an integer from 1 to 10, preferably 3 to 5, and p is an integer from 1 to 5, wherein m+o are at least 4. In other embodiments, the G- and T-rich oligonucleotide has the consensus nucleotide sequence $((G)_x(T)_y)_m(X)_n((T)_y(G)_x)_o$, wherein X is A, T, G or C, each x is independently an integer from 2 to 3, preferably 2, each y is independently 1 or 2, preferably 1, each m is independently an integer from 3 to 5, preferably 4, each n is independently an integer from 1 to 4, preferably 1 or 2, and each o is independently an integer from 3 to 5, preferably 4.

In various embodiments and as mentioned above the oligonucleotide sequence has a length of up to 50 nucleotides, preferably 24 to 30 nucleotides.

In various embodiments the oligonucleotide comprises or consists of the nucleotide sequence $(GGT)_4TG(TGG)_4$ (SEQ ID NO:1).

In various embodiments the oligonucleotide is an ssDNA molecule, optionally modified ssDNA molecule.

The SERS measurements employed according to the present invention, for example in the methods of operating the logic gate, are based on the fact that the G-quadruplex structure is detectable as a local maximum (peak) in the Raman spectrum at a Raman shift in the range of 1470 $cm^{-1}$ and 1500 $cm^{-1}$, preferably between 1480 $cm^{-1}$ and 1490 $cm^{-1}$, more preferably at 1482±3 $cm^{-1}$. In case no G-quadruplex structure is formed or said structure is disrupted, for example by forming the $T-Hg^{2+}-T$ hairpin, no peak at the respective positions can be measured.

A further aspect of the invention relates to a method of operating the logic gate described herein, comprising (a) providing the MetaSERS sensor, wherein the oligonucleotide is comprised in an aqueous solution that is in contact with the split ring resonators; (i) adding potassium ions ($K^+$) and/or (ii) adding mercury ions ($Hg^{2+}$) and/or (iii) adding iodide ions ($I^-$), wherein steps (i), (ii) and (iii) are performed individually or simultaneously and in any order to generate an AND, OR or INHIBIT logic operation; and measuring the SERS signal.

In such a method, the metamaterials, i.e. the split ring resonators may be immersed in the solution comprising the oligonucleotide. The aqueous solution may be any suitable solution, preferably a solution that ensures stability of the oligonucleotide. Preferred are buffered aqueous solutions that contain at least 70 wt. % water, preferably at least 80 wt. %, more preferably at least 90 wt. % water relative to the total weight of the aqueous solution. The solution may contain various salts or buffer substances as well as any auxiliaries that are known and suitable for the described purpose.

According to the described method, the logic gate can be operated to generate an AND, OR or INHIBIT logic operation, depending on the type of ions present in the solution. The ions affect the structure of the oligonucleotide, which can in turn be measured by means of the SERS signal, as will be explained in the following.

Figure 5:
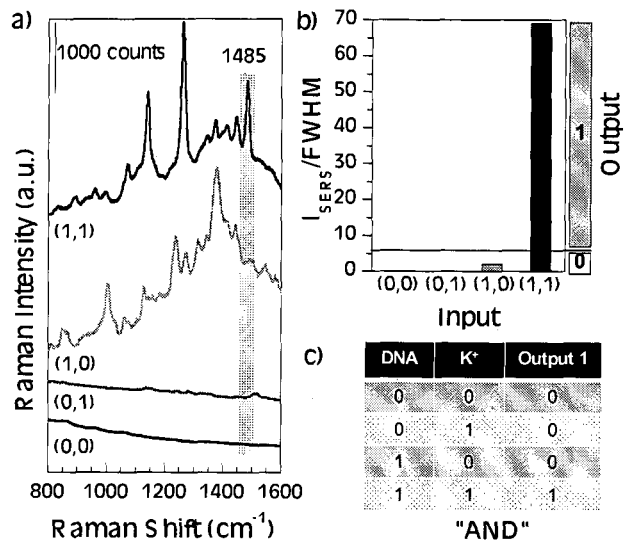
FIG. 5. a) SERS spectroscopy using U45 SRRs surface for the monitoring of Hoogsteen band formation at 1485 $cm^{-1}$ of the GT-rich DNA (2 µM) under coordinating effects of 20 mM $K^+$. b) and c) are normalized Raman intensity changes (ISERS/FWHM) at 1485 $cm^{-1}$ and a truth table for the AND logic gate, respectively.

As already described above, the G-quadruplex structure formed by the oligonucleotide in the presence of potassium ions can be detected in the Raman IR spectrum of the MetaSERS sensor as a peak in the Raman intensity at about 1485 $cm^{-1}$. The increase in this peak in the presence of coordinating cations indicates a first logic state "AND", as it requires the presence of the oligonucleotide and the coordinating cations, such as potassium ($K^+$). The respective output in shown in the truth table in FIG. 5.

Figure 6:
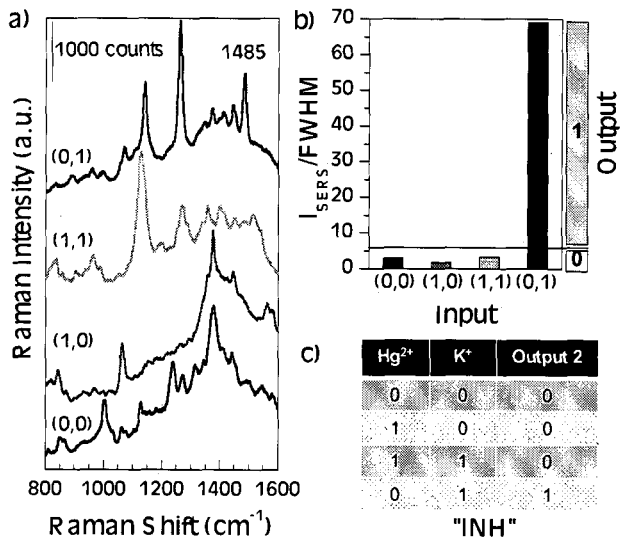
FIG. 6. a) SERS spectroscopy using U45 SRRs surface for the monitoring of Hoogsteen band formation at 1485 $cm^{-1}$ of the GT-rich DNA (2 µM) under coordinating effects of 1 mM $Hg^{2+}$ and 20 mM $K^+$ b) and c) are normalized Raman intensity changes (ISERS/FWHM) at 1485 $cm^{-1}$ and a truth table for the INHIBIT logic gate, respectively.

The addition of mercury ions disrupts the G-quadruplex structure formed by the oligonucleotide in the presence of the coordinating cations ($K^+$) resulting in a decrease of the peak in the Raman spectrum at about 1485 $cm^{-1}$. The decrease in this peak in the presence of coordinating cations and mercury ions indicates a second logic state "INH". The respective output is shown in the truth table in FIG. 6.

The addition of an anion such as iodide that has a higher binding affinity to mercury ions than the nucleotide bases such as thymine, thereby inhibiting the disruption of the Hoogsteen hydrogen bonds and allowing the G-quadruplex to reform, causes an increase in the Raman intensity at about 1485 $cm^{-1}$, when the G-quadruplex (re)forms. The re-occurrence or increase of the signal peak at the respective Raman shift position (at about 1485 $cm^{-1}$) in the presence of coordinating cations, mercury ions and anions such as iodide indicates a third logic state "OR".

To operate the logic gate, the ions necessary to perform the desired logical operation can thus be added in any desired order or combination suitable to achieve the desired structural change of the oligonucleotide. For example, the G-quadruplex may be formed by addition of potassium ions, disrupted by addition of mercury ions, and reformed by addition of iodide ions.

As the logic gate can indicate the present of very small amounts of mercury due to the sensitivity of the formed G-quadruplex structure towards disturbance by complexing of mercury, a further aspect of the invention relates to a method for the detection of mercury ions ($Hg^{2+}$) in a sample using the MetaSERS sensor described herein. The method comprises (a) providing the MetaSERS sensor, comprising alphabetical metamaterials in the form of split ring resonators operating in the wavelength range of from 560 nm to 2200 nm; and the aqueous solution comprising a guanine (G) and thymine (T)-rich oligonucleotide, wherein in the presence of the potassium cations (K$^+$) the oligonucleotide adopts a G-quadruplex structure, and in presence of Hg$^{2+}$, forms a T-Hg$^{2+}$-T hairpin complex that inhibits or disrupts the G-quadruplex structure, wherein the solution is in contact with the split ring resonators, preferably the split ring resonators are immersed in the solution; (b) contacting the MetaSERS sensor with the sample in the presence of potassium ions (K$^+$) under conditions that allow any Hg$^{2+}$ that is present in the sample to form a T-Hg$^{2+}$-T hairpin complex with the oligonucleotide that inhibits formation of or disrupts the G-quadruplex structure; and (c) measuring the SERS signal. The determination of the Raman signal at the Raman shift position indicative for the G-quadruplex structure, i.e. the Raman shift in the range of 1470 cm$^{-1}$ and 1500 cm$^{-1}$, preferably between 1480 cm$^{-1}$ and 1490 cm$^{-1}$, more preferably at 1485 cm$^{-1}$, allows the detection of mercury ions in the sample. As already described above, the G-quadruplex is detectable by SERS as a peak at about 1485 cm$^{-1}$ However, such a structure will only form in the presence of potassium ions and the absence of mercury (II) ions, as mercury (II) ions disrupt the G-quadruplex structure, thus leading to a decrease of the signal or even complete disappearance of the peak signal at about 1485 cm$^{-1}$ in the Raman IR spectrum. This decrease of the Raman intensity may be dependent on the concentration of the mercury ions and can be measured by SERS. As the G-quadruplex structure is very sensitive towards disruption by Hg$^{2+}$ ions and also in view that the SERS technique has a very low detection limit, the described method allows very sensitive detection and optionally also determination of the amount of mercury ions in a sample. The detection limit may be as low as 2×10$^{-4}$ ppb. Generally, concentrations of heavy metals, in particular mercury (as mercury(II) ions), can be detected in a range of 2×10$^{-4}$ to 4×10$^{6}$ ppb, or 2×10$^{-4}$ to 4×10$^{-1}$ ppb, or 2×10$^{-4}$ to 4×10$^{-2}$ ppb, or 2×10$^{-4}$ to 4×10$^{-3}$ ppb.

In various embodiments the sample includes an environmental sample such as from soil, water, waste sites or any plant, animal, fungal or bacterial sample. Depending on the sample type, it can be determined whether there is mercury contamination at a given site or a given organism is suffering from high loads of mercury. In various embodiments, the sample includes a food sample. Food samples may include but are not limited to processed or fresh fish, milk powder, health supplements or any other type of food suspected to have high concentrations of heavy metals such as mercury. In various embodiments the sample includes a biological sample. The biological sample may include an extract from any plant, animal, fungal or bacterial species.

A further aspect of the invention relates to a device comprising the logic gate as described herein.

In various embodiments the device is a biosensor. The biosensor can be used for clinical diagnostics, environmental monitoring, food safety analysis whereby the presence of heavy metals such as mercury can be detected at low concentrations, as defined above.

A further aspect of the invention relates to the use of a logic gate as described herein. The logic gate can be used for computations such as biological computations and may, according to such a use, be operated as described above for the corresponding method.

A further aspect of the invention relates to use of a logic gate as described herein for mercury ion (Hg$^{2+}$) detection in a sample as described above.

It should be understood that all embodiments disclosed above in relation to the logic gate or methods of the invention, are similarly applicable to the inventive methods and uses and vice versa.

As already described above, the present invention thus features the construction of a label-free and switchable molecular logic gate that uses specific conformation modulation of a guanine- and thymine-rich DNA, while the optical readout is enabled by the tunable alphabetical metamaterials, which serve as a substrate for surface enhanced Raman spectroscopy (MetaSERS). The present invention therefore presents a comprehensive solution to tailor the plasmonic responses of MetaSERS with respect to the metamaterial geometry, excitation energy, and polarization, as identified by computational and experimental investigations. The tunable MetaSERS-based DNA logic is simple to operate, highly reproducible, and can be stimulated by ultra-low concentration of the external inputs, enabling an extremely sensitive detection of mercury ions.

It has been demonstrated that tuning the Vis-NIR alphabetical metamaterials modulates the optical response and hot-spots leading to an ultrasensitive SERS detection. According to the inventive methods and uses, INHIBIT and OR logic gate operations based upon the metallophilic properties of a guanine- and thymine-rich oligonucleotide sequence to K$^+$ or Hg$^{2+}$ ions, which can specifically trigger or interrupt the formation of Hoogsteen hydrogen bonding, can be monitored by means of MetaSERS with high sensitivity and selectivity. Significantly different from many other fluorescence-based or DNAzyme-based logic gate operations which involve complex handling and analysis procedures, the MetaSERS is a direct measurement and can be implemented without the need of any labeling fluorescent dyes or enzymatic activities. Moreover, the molecular logic enables the ultrasensitive detection of mercury ions at a concentration as low as 2×10$^{-4}$ ppb, which is at least 3 orders of magnitude improvement compared to concentrations reported in the literature.

In summary, it has been demonstrated that the Vis-NIR tunable alphabetical metamaterials have unique ability for optically controlling the hot-spots. The optical response can be readily tuned in Vis-NIR range by tailoring the size and shape of the resonators. Also demonstrated for the first time is the use of metamaterials as SERS-based logic gate operations and for the detection of mercury ions with ultrahigh sensitivity and selectivity based on the specific conformation modulation of a GT-rich oligonucleotide. The most notable attributes of the MetaSERS-based logic gates developed in this effort are their label-free measurement, sensitivity, reversibility, reproducibility, and simplicity. The novel concept of using MetaSERS represents a new approach for molecular logic gates that can be possibly operated down to single molecule level, and will be beneficial for a variety of applications such as clinical diagnostics, environmental monitoring, food safety analysis, and biological computations.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples.

EXAMPLES

Example 1: Fabrication of Alphabetical Metamaterials

The metamaterials with different bar widths from 30 to 80 nm were fabricated on 0.7 mm-thick ITO/glass substrates over an area of 40 μm×40 μm by electron beam lithography (EBL). Any other substrates known in the art would also be suitable. Commercial electron beam resist polymethyl methacrylate was spin-coated at 4,000 rpm for 1 min on the ITO/glass, and baked at 180° C. for 20 min.

The metamaterials patterns were produced using a JEOL 7001 F SEM equipped with a nanometer pattern generation system (NPGS), and then developed in 1:3 methyl isobutyl ketone:isopropyl alcohol (MIBK:IPA) developer for 90 s. After the development, 30 nm Au film following a 2-nm Cr as an adhesive layer was deposited using thermal evaporation deposition (Elite Engineering, Singapore) at a base pressure of 3×10$^{-7}$ Torr. Finally, the sample was immersed in acetone for at least 3 hr for lift-off, and washed thoroughly with IPA and water.

Example 2: Resonance Modes Identification of Alphabetical Metametrials

Figure 10:
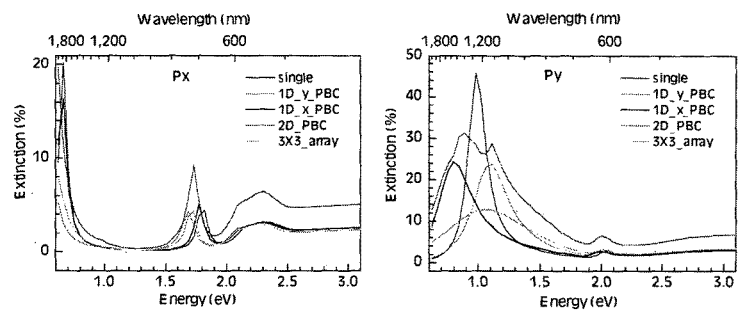
FIG. 10. Simulated extinction spectra depending on the dimensions of selected metamolecule units. The demonstrated metamaterials is the H shape with bar-width w=30 nm. The $P_x$ and $P_y$ are the polarization directions of incident light along to the x- and y-directions, respectively. The red line is simulated by single metamolecule unit cell. The green and blue lines are simulated by the one dimensional periodical boundary condition along to y- and x-directions, respectively. Pink line is simulated by two dimensional periodical boundary conditions. Cyan line is simulated by three-by-three array unit cells.

FIG. 1 shows a series of alphabetical metamaterial structures (FIG. 1a), their optical responses (FIG. 1b), and mode identification (FIG. 1c). In order to obtain the tunable optical response from Vis to NIR range, the whole unit cell was minimized along with the dimension of resonators from 100% to 37.5%, which reduces the corresponding bar width (w) from w=80 to 30 nm. FIG. 1b shows the transmission spectra for various alphabetical metamaterials with different widths. The solid curves are spectra taken under $P_x$ polarization configurations, while the dashed curves are obtained from $P_y$ polarization configurations. Each valley in the transmission spectra represents one resonance mode of metamaterials. The induced electric dipoles due to the alternating field of light lead to two kinds of resonance modes: one is electric mode arising from oscillation of the electric dipoles, while the other is the magnetic mode due to the circular currents induced by head-to-end electric dipoles configuration. For all five shapes, the weak short-wavelength resonances around 550 nm exhibit independence on the width, which are actually attributed as the dipole excitation along the width of arms. The other resonance modes exhibit a systematic blue shift as the width decreases, labeled with color lines as guide to eye. This can be explained as follows. For electric modes, resonance frequency is proportional to the coupling strength of electric dipoles with a decreasing of the meta-molecule width, the coupling strength and thus the resonance frequency increase. The magnetic mode can be seen as the analogy of inductor-capacitor circuit (LC) resonance. With the decrease of the meta-molecule size and bar width, the capacitance C and inductance L decrease and the resonance frequency increases. FIG. 1c shows the schematic diagram of the current distribution at the resonance wavelength based on the simulation of discrete dipole approximation (DDA) and dipole-dipole coupling theory. The black arrows in FIG. 1c indicate the current direction. The detailed DDA simulation results of 30 nm width are shown in FIG. 10. The simulated mode numbers, polarization and relative energy are in good agreement with experimental results within 10% deviation.

The physical origin of all the labeled modes was identified. The U shape resonator is a typical SRR and has been extensively studied due to its negative refractive properties. It has three resonance modes from high to low energy as shown in FIG. 1c: the higher order magnetic resonance (Mh-order modes, highlighted by the solid blue line in FIG. 1b), fundamental electric resonance (E(y) modes, highlighted by dash green line in FIG. 1b, y represents the polarization direction of incident light), and fundamental magnetic modes (M(z), highlighted by solid red line in FIG. 1b, z represents the direction of magnetic dipole moment). Here, the highest frequency mode was identified as the higher order magnetic resonance rather than electric plasmon mode because it has a partial circular current, leading to a magnetic-dipole moment as shown in FIG. 1c and FIG. 10. Based on the simulation shown in FIG. 10, it was concluded that Mh-order and M(z) modes can only be excited at the $P_x$ polarization configuration (electric field vector of incident laser is along the x-direction) while E(y) mode can only be probed at the $P_y$ polarization configuration.

Figure 11:
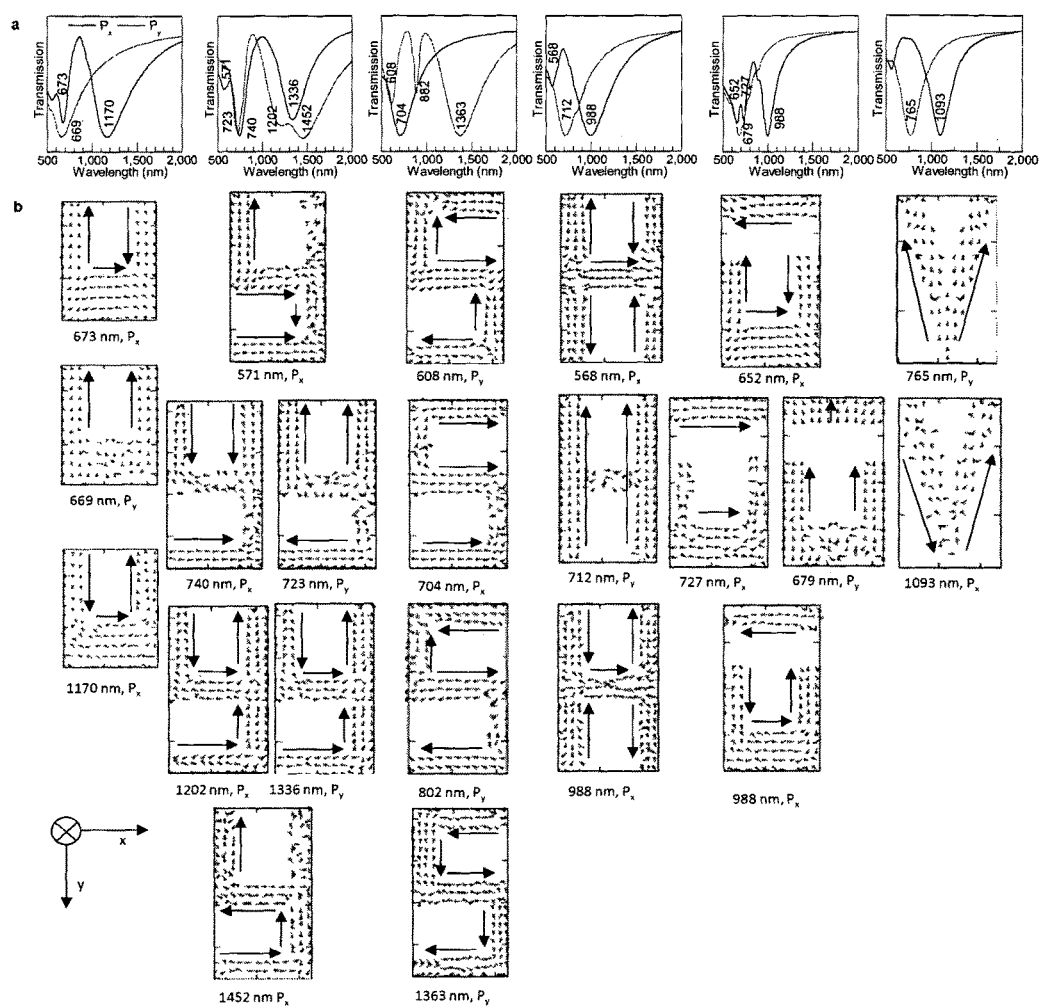
FIG. 11. DDA simulation of transmission spectra and corresponding dipole current distributions. a, the simulated transmission spectra of U, Y, S, H, U-bar and V shapes (from left to right) with a bar-width w=30 nm and a thickness of 60 nm. The 60 nm thickness was chosen in order to make the simulated gold film attributable to more scattering to match the real scattering in evaporated non-crystalline gold film. b, the dipole current distributions of different resonant peaks in a. the $P_x$ and $P_y$ are the polarizations of incident light along x- and y-directions, respectively.

The analysis of U-shaped resonator can be applied to interpret the other shapes. For instance, the Y-shaped resonator can be regarded as two connected U-shaped resonators rotated by a 90°. The modes in the isolated U-shape will couple together and lead to new modes in the composite shapes. The solid blue line highlights the size dependent evolution of the coupled higher order magnetic mode Mh-order, which is induced by $P_x$ polarized light and shows more complex current distribution as shown in FIG. 1c and FIG. 11b. The $P_x$ and $P_y$ polarization of incident light induce a couple of degenerated electric mode Esym(x) and Esym(y) corresponding to the valleys highlighted by the green solid and dashed lines in FIG. 1b, respectively. This is supported by the simulation depicted in FIG. 11. However, experimentally it was observed that the mode splitting as the Y-shaped resonator size increases, which are highlighted by the green solid and dashed lines in FIG. 1b. It is speculated that as the size increases the degeneracy is lifted due to non-ideal symmetry of the two U-shaped resonators. For magnetic modes, the fundamental magnetic dipole modes in each U-shaped resonator couple together, resulting in the two degenerate symmetrically coupled magnetic dipoles modes ($M_{sym}$,x(z) and $M_{sym}$,y(z)) and one asymmetric mode $M_{asym}$ (Z) As there is a phase retardation between two 90°-rotated U shapes, the coupling between two magnetic dipoles leads to the spectral splitting of resonance. Based on the dipole-dipole coupling theory, the north and south poles of the two neighboring magnetic dipoles repel each other in the symmetric mode, leading to the longer wavelength $M_{asym},y(z)$ mode as highlighted by the dashed red line in FIG. 1$b$ under a $P_y$ excitation, which is further red shift beyond the range of the spectrometer in resonator sized larger than ~60 nm. In a P polarization excitation, only $M_{sym},x(z)$ mode is observed as highlighted by solid pink line in FIG. 1$b$. With a similar argument, the spectra of coupled magnetic modes ($M_{sym},x(z)$ and $M_{sym},y(z)$) also split into two with the increasing of the size. Similar analysis can be applied to S, H, U-bar, and V shaped resonators.

Figure 2:
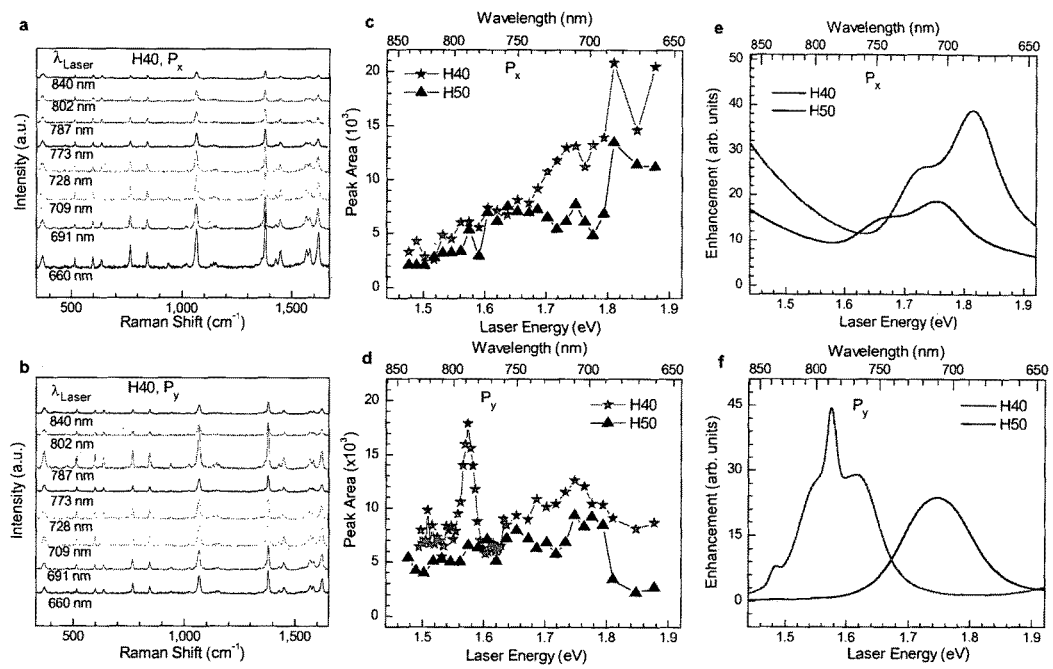
FIG. 2. Excitation wavelength dependence of experimental SERS spectra and simulated enhancement spectra at $P_x$ and $P_y$ polarization. a and b, are the selected measured SERS spectra depends on the laser wavelength for H40 at $P_x$ and $P_y$ polarizations. c and d, are laser energy dependence of the integrated area intensity of ring-ring stretching mode of benzene functional groups at 1,380 $cm^{-1}$ for H40 and H50 pattern at two polarization configuration. e and f, are the simulated enhancement of SERS signal corresponding to the c and d. The enhancement factor value was calculated from the product of enhancement factors at the laser wavelength and that at the scattering wavelength, i.e. $EF=E^2(\lambda_{laser}) \times E^2 (\lambda_{scattering})$. The scattering peak is 1,380 $cm^{-1}$.

Example 3: Maximization of the SERS Enhancement by Tuning the Laser Wavelength Alphabetical metamaterials operated in visible-NIR exhibit abundant electric and magnetic dipole modes, and their coupling effect gives further degree of freedom to tune the plasmonic resonance to optimize the SERS effect. The versatile tunability enables the maximization of the strength of local electromagnetic field hot-spots, which dominate the electromagnetic enhancement in SERS effect. It was first shown that the highest SERS signal can be obtained by tuning the laser wavelength using H-shaped metamaterials as an example. FIGS. 2$a$ and 2$b$ display the typical SERS spectra of a monolayer 2-naphthalenethiol bound to H40 sample excited by a tunable laser with $P_x$ and $P_y$ polarizations, respectively. Considering that laser wavelength (660-840 nm) is far from the first electronic transition (~242 nm) of 2-naphthalenethiol, it is hypothesized that the enhancement of SERS signal is entirely contributed by the electromagnetic enhancement. The Raman peak around 1,380 cm$^{-1}$ originated from the ring-ring stretching mode was chosen to investigate the resonant SERS profile depending on the laser wavelength. Its integrated area intensity is plotted in FIGS. 2$c$ and 2$d$ along with comparison data from H50 sample. By tuning the laser wavelength and polarization to match the corresponding resonant modes in metamaterials, the enhancement was obtained about 20 times as compared to that of the off-resonance case. Based on the Mie scattering theory, the electromagnetic enhancement factor (EF) is the product of incident light and scattered light enhancement, i.e. $EF_{total}=EF(\lambda_{laser}) \times EF(\lambda_{scatt})$, where $EF(\lambda)$ has the same dispersion relationship with the extinction spectra of metamaterials. In the case of $P_x$ polarization, the $M_{h\text{-}order}$ M (~730 nm for H40, and ~820 nm for H50) and $M_{asym}(y)$ (~1561 nm for H40, and ~1898 nm for H50) were excited (as show in FIG. 1$b$). Because the $M_{asym}(z)$ mode is far from the excitation laser and the corresponding stokes shift (1,380 cm$^{-1}$), the stronger signal at higher energy excitation shown in FIG. 2$c$ is due to the $M_{h\text{-}order}$ resonance. While in the $P_y$ excitation, two other modes of $E_{sym}(y)$ (~780 nm for H40, and ~900 nm for H50) and $E_{asym}(y)$ (~860 nm for H40, and ~1150 nm for H50) are excited. As shown in FIG. 2$d$, two resonant peaks are observed in the H40 sample. One resonant peak is very sharp at around ~790 nm with a FWHM of ~10 nm. It is proposed that it is a double resonant process, in which the incident laser at ~785 nm resonates with $E_{sym}(y)$ while the scattered light at ~887 nm (~1,380 cm$^{-1}$) also within the resonance of the $E_{asym}(y)$ mode. The other peak around 710 nm is much broader because only the scattered light around 787 nm (1,380 cm$^{-1}$) can resonate with the $E_{sym}(y)$ mode. For H50 sample, the double-resonance is relaxed, which results in one broad resonant peak around ~700 nm because its $E_{asym}(y)$ mode is too broad and far from the scattered light. Accordingly, the resonant profiles of enhancement have been calculated by multiplying the simulated $|E/E_0|^2$ of the extinction spectra at the incident laser wavelength and the scattered light wavelength for the 1,380 cm$^{-1}$ mode, for both H40 and H50 samples. The results are shown in FIGS. 2$e$ and 2$f$. As can be seen, the simulated results are qualitatively in good agreement with the experimental results. The difference may come from the relative deviation of resonance peak position between experiments and theory.

Figure 3:
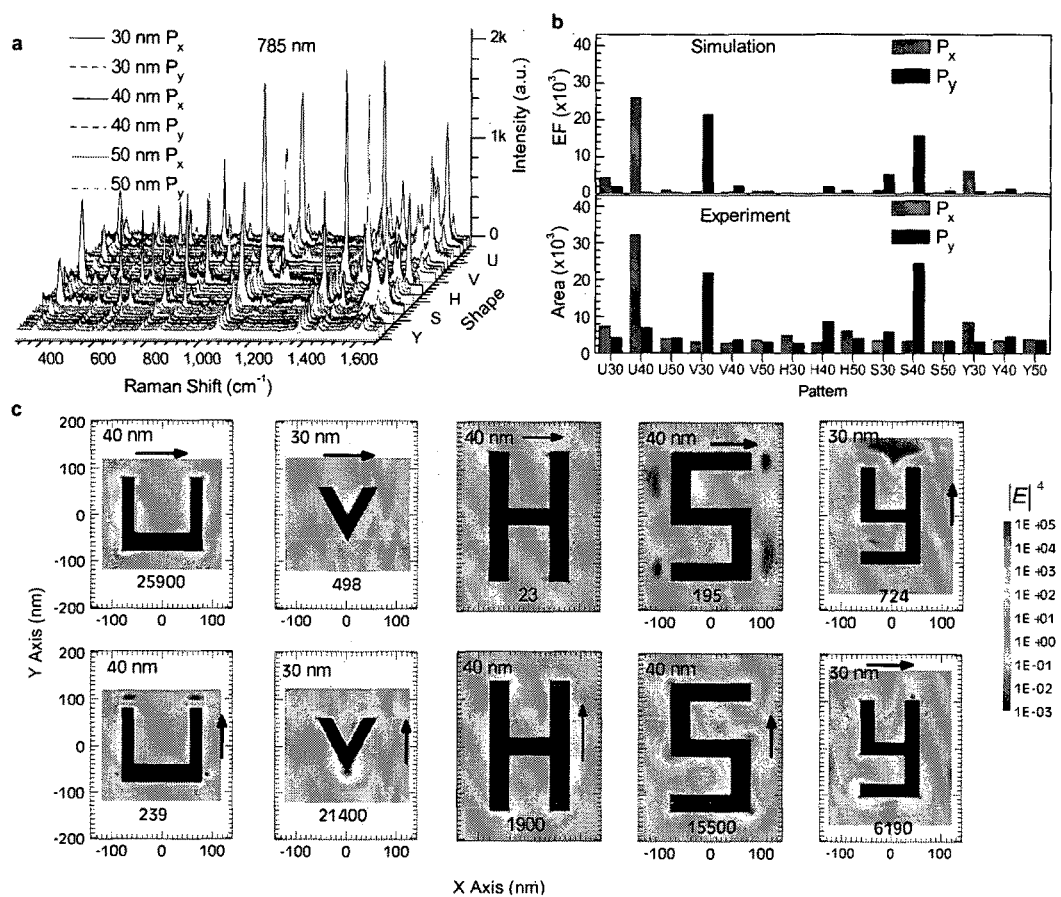
FIG. 3. Shape tunable SERS spectra and simulation results at 785 nm excitation. a. The experimental SERS spectra depending on the shape and width (w=30 nm for red line, w=40 nm for blue line, w=50 nm for pink line) of the alphabetical metamaterials at 785 nm laser with two cross-polarization configurations. The solid lines and the dash lines represent for the laser polarizations which are parallel and vertical to the gap of the alphabet metamaterials, respectively. b. The statistics results of experimental SERS spectra in a and simulated average enhancement factor for S, H and Y shapes from w=30 nm to w=50 nm with two polarization configurations. c. The simulated contour plot of SERS enhancement factor $|E|^4$ distribution for the pattern with the highest enhancement. The black arrows correspond to the laser polarizations. The right corner values are the width w of the SRRs unit, and the bottom values are the average enhancement factor.

Example 4: Maximization of the SERS Enhancement by Tuning the Shape and the Size of Metamaterials For a given laser wavelength, for instance 785 nm, the enhancement can be maximized by tuning the size and shape of the alphabetical metamaterials. In this context, the chosen patterns are U, V, H, S and Y shaped metamaterials with bar-width from 30 to 50 nm, also functionalized with a layer of 2-naphthenethiol molecules. FIG. 3$a$ shows a 2D plot of the SERS spectra under two different polarizations. Bar charts in FIG. 3$b$ statistically summarize the simulated and experimental intensities for all different shapes and sizes. It becomes pronounced that the U40, V30, H40, S40 and Y30 samples show much stronger intensities than their other counterparts under a certain polarization. This suggests the versatility and tunability of metamaterials for a known laser excitation in order to gain the highest SERS effect. The explanation can be supported by the simulation of the local electric field contour distribution (or saying the hot-spots) as shown in FIG. 3$c$. Both experimental data and simulation agree very well with each other. For the 785 nm laser, the simulated highest and average enhancement factors are $\sim 3 \times 10^6$ (V30 for $P_y$ polarization) and ~25,900 (U40 for $P_x$ polarization). By comparing the Raman spectra of 2-naphthalenethiol powder and the SERS spectra of a covalently self-assembled monolayer of 2-naphthalenethiol, it was possible to also estimate the average enhancement factors (averaging all area of metamaterials pattern) of experimental SERS spectra which are $\sim 10^6$ to $\sim 10^8$, respectively. See FIG. 13. These enhancement values are strong enough for detecting a few molecules located within proximity of the hot-spots.

Example 5: Construction of DNA Logic Operations

Figure 4:
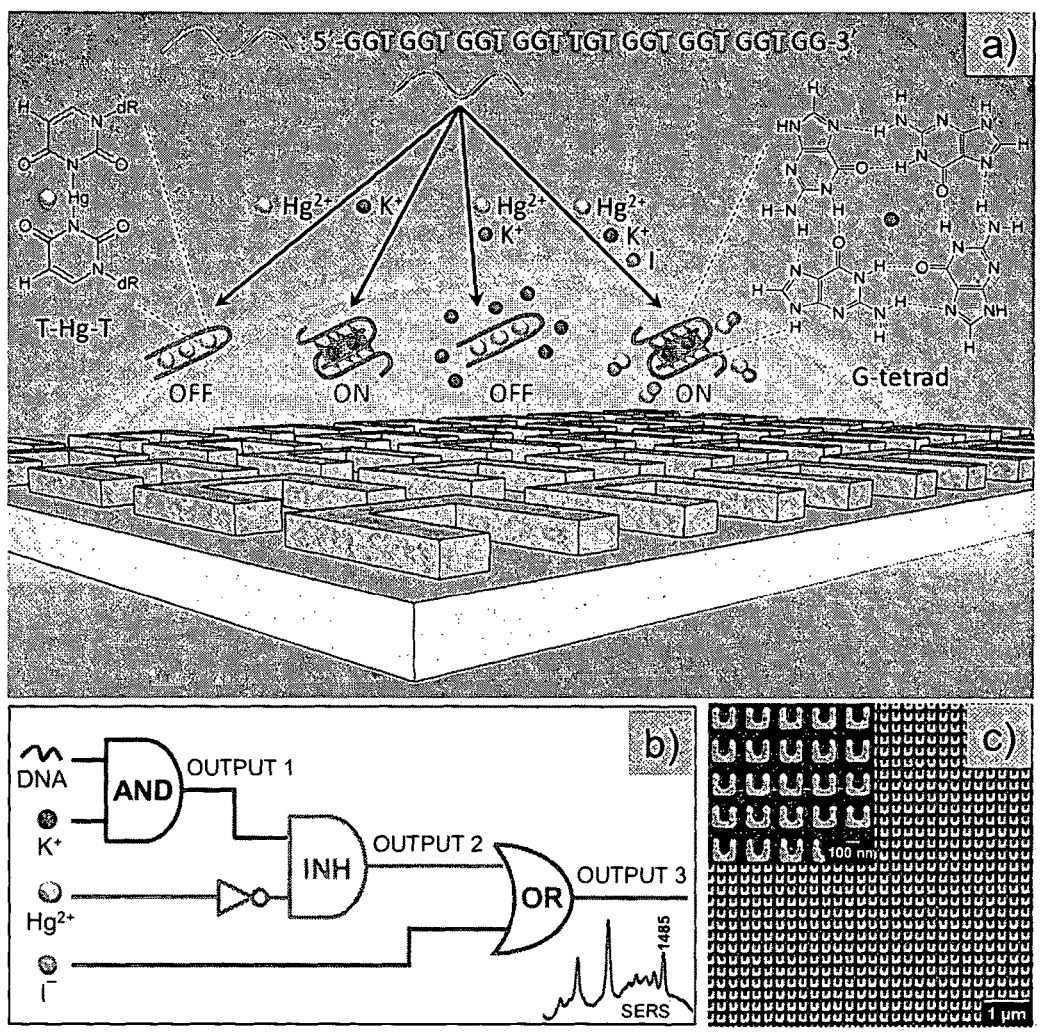
FIG. 4. Combinational logic gate operations (AND, INH, and OR) using metamaterials-generated SERS. a) Schematic illustration of the Hoogsteen hydrogen bonding activation using the GT-rich oligonucleotide, $Hg^{2+}$, $K^+$, and $I^-$ ions as inputs. The output is translated into "ON" or "OFF" states of SERS signal at ~1485 $cm^{-1}$, which is a diagnostic marker of the C8=N7-H2 Hoogsteen hydrogen bonding of the folded G-quadruplex structure. b) Network map schematically represents the combination of AND, INHIBIT and OR gates for the switchable logic operations. c) SEM micrograph represents uniform and reproducible fabrication of U40 SRRs used as the SERS substrate. Inset is a magnified image, average width of the SRRs w=45.2±2.6 nm.

The U40 metamaterials provided the highest electromagnetic enhancement as excited by a 785 nm laser. Such strong enhancement allows the alphabetical metamaterials to be exploited as DNA molecular logic circuits based upon SERS effect. As shown in FIG. 4, the principle of the logic operations is based on the sequentially coordinating effects of $Hg^{2+}$ and $K^+$ on the conformational modulation of a short guanine (G)- and thymine (T)-rich oligonucleotide sequence $((ggt)_4tg(tgg)_4)$. In the presence of $K^+$ cations, G-rich oligonucleotides are known to fold into a specific and stable three-dimensional shape, namely G-quadruplex where four G can self-assemble to form a distinct Hoogsteen hydrogen-bonded square (i.e. G-tetrad or G-quartet) via C8=N7-H2. The Hoogsteen hydrogen bonding results a sharp and strong peak centered at ~1485±3 cm$^{-1}$ as measured by Raman scattering spectroscopy. On the other hand, $Hg^{2+}$ cations have been demonstrated to bridge specifically with two thymines by labile covalent bonds via N—$Hg^{2+}$ to form a hairpin T-$Hg^{2+}$-T complex with a binding constant of ~8.9×

$10^{17}$ M$^{-1}$, which is much higher than that of K$^+$ cations stacking with the quadruplex structure (~5×10$^6$ M$^{-1}$). Therefore, it provides a rationale for a DNA-based detection of Hg$^{2+}$ in which the formation of T-Hg$^{2+}$-T complex in the presence of Hg$^{2+}$ will inhibit the formation of G-quadruplex structure that in turn leads to the diminishment of the diagnostic Hoogsteen hydrogen bonding at ~1485 cm$^{-1}$. In addition, it has been previously reported that the binding constant of Hg$^{2+}$ ions and iodide (I$^-$) is as high as 5.6×10 (Lee et al. Angew. Chem. Int. Ed. 47, 4093-4096 (2007)), therefore the introduction of I$^-$ could competitively disrupt the T-Hg$^{2+}$-T bonding and lead to the reversible formation of the Hoogsteen band under the presence of K$^+$. This will generate reversibly the combinational AND, INHIBIT and OR logic gates schematically represented in FIG. 4b. FIGS. 5a and 5b depicts the interaction of GT-rich DNA and K$^+$ inputs for the development of a SERS-based AND logic gate operation using the U40 SRR as a substrate. The presence and absence of GT-rich DNA or K$^+$ input are defined as 1 and 0, respectively. The intensity of Raman band at ~1485 cm$^{-1}$ normalized by its full width at half maximum (FWHM) is represented for the output 1 or 0. The combinations of four possible inputs are listed in the truth table (FIG. 5c). The bare U45 SRRs (0,0) and the addition of K$^+$ buffer (0,1) do not generate any noticeable SERS modes. When the GT-rich DNA prepared in K$^+$-free buffer is introduced (1,0), strong Raman bands at 860, 1005, 1128, 1274, 1237, 1374 cm$^{-1}$ have been observed, and only weak hydrogen bonding of the Guanine N7 centered at 1492 cm$^{-1}$ is present. However, in the presence of both GT-rich DNA and K$^+$ buffer (1,1) the strong Hoogsteen band at ~1485 cm$^{-1}$ is generated, giving rise to the true value of output. This leads to the formation of AND logic operation as shown in the truth table (FIG. 5c). The assignment of a few other strong peaks in the SERS spectra is discussed in detail in other work.

The INHIBIT molecular logic gate is presented in FIGS. 6a and 6b, where the DNA is kept constantly, and the presence and absence of Hg$^{2+}$ or K$^+$ input are respectively defined as 1 and 0. The combinations of four possible inputs are listed in the truth table (FIG. 6c). In the absence of inputs (0,0) or with the Hg$^{2+}$ alone (1,0), the GT-rich oligonucleotide is respectively in its unfolded state or in complexed form with T-Hg$^{2+}$-T, and therefore no strong Hoogsteen band is observed. The intensity of the Hoogsteen hydrogen band is significantly increased when the K$^+$ ions are introduced (0,1), giving rise to the output of 1. However, the band at ~1485 cm$^{-1}$ is completely diminished in the presence of both inputs (1,1), meaning that the coordination of Hg$^{2+}$ in the T-Hg$^{2+}$-T complex inhibits the formation of the Hoogsteen hydrogen bonding.

Figure 7:
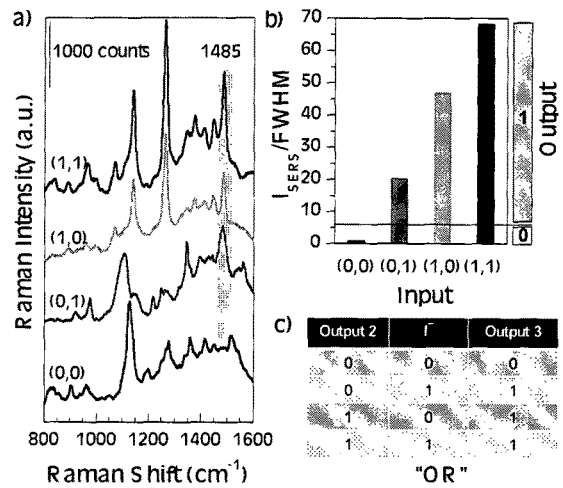
FIG. 7. a) SERS spectra show that formation of the Hoogsteen band is switchable upon the introduction of 50 mM iodide anion (I⁻). The normalized Raman intensities at 1485 cm$^{-1}$ are plotted in b), and c) is a truth table for the OR logic gate operation.

As a means to evaluate the reversibility of the Hoogsteen hydrogen bonding, I$^-$ ions are subsequently introduced to the logic operation (FIG. 7). In this case, the output of the INHIBIT logic gate (output 2) is used as one of the inputs. FIGS. 7a and 7b show the SERS spectra and the normalized Raman intensities at ~1485 cm$^{-1}$ for monitoring the reformation of the Hoogsteen band. It should be noted that K$^+$ has been already introduced in the buffer solution, thus G-quadruplex formation will be generated as long as the free GT-rich DNA is present. I$^-$ ions strongly bind with Hg$^{2+}$ to break the bridge between thymine and Hg$^{2+}$ and to liberate the GT-rich oligonucleotide in such a way that the G-quadruplex could be reformed by stacking with K$^+$. Therefore, in the absence of inputs (0,0) the T-Hg$^{2+}$-T complex could not be disrupted, resulting in the output 3 of 0. However, the output 3 is true if either the output 2 or I$^-$ ion is true ((0,1), (1,0), or (1,1)), leading to an OR logic operation as shown in the truth table (FIG. 7c).

Figure 8:
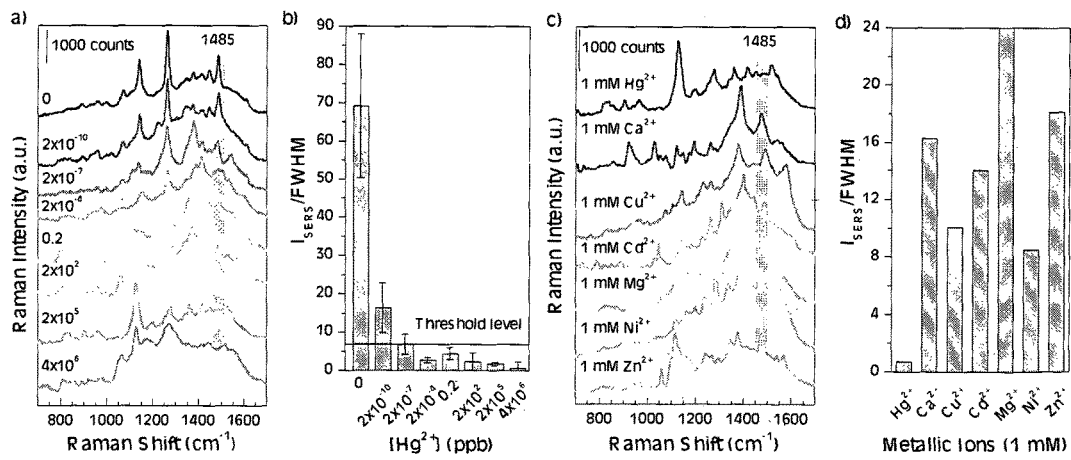
FIG. 8. Highly reproducible SERS spectra generated by the metamaterials for the detection of mercury ions. a) SERS spectra of the GT-rich oligonucleotide under coordination of various concentrations of $Hg^{2+}$ ranging from 0 to 4×106 ppb. The diagnostic Hoosteen band intensities at ~1485 cm$^{-1}$ show an inverse relationship with the $Hg^{2+}$ concentrations. b) Statistic data represent the correlation of normalized SERS intensities at ~1485 cm$^{-1}$ as a function of $Hg^{2+}$ concentrations for three parallel acquisitions. c) SERS spectra of the GT-rich oligonucleotide treated with various metallic ions at 1 mM concentration. d) The normalized SERS intensities at 1485 cm$^{-1}$ indicate that the mercury ions were clearly differentiated from other cations at the same concentration.

Example 6: MetaSERS-Based DNA Logic Gate for Ultrasensitive Detection of Mercury Ions The principle of molecular logic gates discussed in FIG. 4 presents a rationale for ultrahigh sensitive detection of Hg$^{2+}$ ions: the trace amount of Hg$^{2+}$ ions bind to the GT-rich oligonucleotides to form hairpin structures thus strongly inhibiting the formation of the quadruplex structures. As a result, the 1,485 cm$^{-1}$ Raman fingerprint of the Hoogsteen hydrogen bonding diminishes. This suggests that lower Hg$^{2+}$ ion concentration actually leads to a stronger the Raman fingerprint band. FIG. 8a shows the representative SERS spectra of the GT-rich oligonucleotide under coordination of various concentrations of Hg$^{2+}$ ranging from 0 to 4×10$^6$ ppb, where the Hoogsteen bands at ~1,485 cm$^{-1}$ are inversely proportional to the Hg$^{2+}$ concentrations. The intensities were normalized and plotted statistically as shown in FIG. 8b where a threshold level is defined as three times of standard deviation from the blank sample is used to identify detection limit of the assay (L.O.D). The bar graph indicates that concentrations of Hg$^{2+}$ ranging from 2×10$^{-4}$ to 4×10$^6$ ppb could be detected, and the lowest detectable concentration (2×10$^{-4}$ ppb) is four orders of magnitude lower than the exposure limit allowed by EPA. Strikingly, the detection limit of the assay far exceeds all reported sensitivity of Hg$^{2+}$ detections, including the L.O.D of 20 ppb or 2 ppb for colorimetric detections using DNA-functionalized gold nanoparticles, 0.2 ppb for DNA-based machine or fluorescence polarization enhanced by gold nanoparticles.

Different metallic ions (such as Ca$^{2+}$, Cu$^{2+}$, Cd$^{2+}$, Mg$^{2+}$, Ni$^{2+}$, Zn$^{2+}$) have been used to investigate the selectivity of the logic gate. The results in the FIG. 8c show that these metallic ions are far less effective at preventing the formation of Hoogsteen hydrogen bonding, their corresponding normalized Hoogsteen band intensities are much higher than that of the Hg$^{2+}$-treated sample (FIG. 8d). Therefore, the MetaSERS based logic gate has not only ultrahigh sensitivity but also good selectivity for the detection of Hg$^{2+}$.

Materials and Methods

Transmission and SERS Measurements.

To evaluate the resonance modes of alphabetical metamaterials, the transmission spectra were conducted using a microspectrophotometer in the range of 400-2,100 nm. The laser tunable SERS spectroscopy was performed in a back scattering geometry using a Jobin-Yvon HR800 Raman system equipped with a liquid nitrogen-cooled charge-coupled detector (CCD). The laser excitation wavelengths are selected from a Ti-Sapphire laser (Coherent). For pattern tunable experiments (FIG. 3), Jobin-Yvon T64000 was used in a back scattering geometry excited by a diode laser ($\lambda$=785 nm). For all SERS experiments, the laser power was kept bellow 1 mW otherwise stated. For the laser tunable SERS spectroscopy (FIG. 2), an important step is to calibrate the wavelength-dependent laser flux and the equipment response. A silicon wafer with <111> orientation was used as a standard sample for the calibration of the laser flux, while a standard tungsten halogen light source (HL-2000, Ocean Optics) was used to calibrate the equipment response.

Discrete Dipole Approximation Simulation.

The electric-magnetic field of alphabetical metamaterials is simulated by discrete dipole approximation (DDA)

method using the DDSCAT program (version 7.0). 2-nm grids were used for all simulations.

Operation of MetaSERS-Based Logic Gates.

The GT-rich DNA (10 μM) was first heated to 90° C. for 10 min and then immediately chilled in ice water for 2 hr. For the INHIBIT logic gate, final effective concentrations of the pretreated GT-rich DNA (2 μM) was then added into different solutions: HEPES buffer (input=0, 0), HEPES buffer plus 1 mM $Hg^{2+}$ (input=1, 0), HEPES buffer plus 1 mM $Hg^{2+}$ and 20 mM $K^+$ (input=1, 1), HEPES buffer plus 20 mM $K^+$ (input=0, 1). For an OR logic gate operation, an additional amount of 50 mM $I^-$ ion was subsequently introduced into thea samples. The samples were then incubated for 2 hr at room temperature. Subsequently, an aliquot of the reacted solutions containing the GT-rich DNA and ions was dropped onto the U-shaped SRR substrate. Then, a glass coverslip (thickness no. 1) was placed on the SRR substrate and sealed with parafilm stripes to avoid evaporation. SERS measurement was performed on the SRR substrates using a micro-Raman spectrometer (Horiba-JY T64000) excited with a diode laser ($\lambda$=785 nm) in the backscattering configuration. The back scattered signal was collected through a 50× objective lens, the laser power on the sample surface was measured about 2.5 mW, and acquisition time was 50 s.

For the sensitivity and selectivity experiments, volumes containing final effective concentrations of 2 μM preheated GT-rich DNA, HEPES buffer (50 mM HEPES buffer pH 7.4, 0.1% Triton X-100, 2% dimethyl sulfoxide), and each concentrations of $Hg^{2+}$ ranging from 0 to $4\times10^6$ ppb were incubated for 2 hr at room temperature. For evaluating the selectivity, various metallic ions at 1 mM concentration ($Ca^{2+}$, $Cu^{2+}$, $Cd^{2+}$, $Mg^{2+}$, $Ni^{2+}$, $Zn^{2+}$) were used instead of $Hg^{2+}$. The samples were also incubated for 2 hr at room temperature before the SERS analyses as described above.

Mode Identifications: S, H, U-bar, and V Shaped Resonators

Identifications for the mode identifications for other four resonators. The S and H shaped resonators can be considered as two 180°-rotated U-shaped resonator configurations connected side-by-side and back-to-back, respectively. The electric (magnetic) dipole-dipole coupling can also form new coupled electric (magnetic) modes. In the S shape, four resonance modes were observed as highlighted by solid blue, dash green, dash pink and solid red lines in FIG. 1b, which are respectively identified as higher-order magnetic resonance mode M h-order, symmetrically coupled electric modes $E_{sym}(x)$ and asymmetrically coupled electric modes $E_{asym}(x)$, and asymmetrically coupled magnetic mode $M_{asym}(z)$ as shown in FIG. 1c. The $E_{asym}(y)$ mode is very weak and even unresolved when the bar-width is smaller than 50 nm, however it becomes pronounced for larger size resonators (highlighted by pink dashed line). In H shape, besides $M_{h\text{-}order}$, $E_{sym}(Y)$ and $M_{asym}(z)$ modes, an asymmetrically coupled electric mode of $E_{asym}(y)$ in the $P_y$ polarization excitation was also observed, which is completely dark and decoupled from the normal incident light if the metamolecule exhibits spatial inversion/reflection symmetry, such as the U shape, in the plan of structure[1]. It is proposed that the observation of $E_{asym}(y)$ in the H-shaped metamaterial is due to the coupling effects between two U shapes. As there is no phase retardation between the two 180°-rotated U pairs, only a single asymmetric magnetic resonance can be observed in the S and H shapes. The U-bar structure is also known as asymmetric split ring resonators (ASRRs). It consists of a SRR and a bar. The higher order magnetic resonance $M_{h\text{-}order}$ shows asymmetric alignment of electric dipoles in both of two vertical arms of SRR, and in both of the bar and the bottom arm of SRR. The electric resonance mode is contributed from two degenerated modes of $E_{sym}(x)$ and $E_{sym}(y)$ with parallel alignment of electric-dipoles along x- and y-direction, respectively. Circulating currents induced by $P_x$ polarized incident light lead to the magnetic resonance M(z). For the V shape, two resonance modes come from the coupling of two dipoles in the angled arms. The $P_y$-polarization of light induces symmetric aligned electric diploes in two arms, resulting in an electric mode E(y). Similar with asymmetric coupling in two non-contacted nanowires, the displacement current of asymmetric coupled dipoles between two arms of the V shape also has partial circulating features along the V shape, leading to a resonant excitation of magnetic dipole moment M(z).

DDA Simulation

Simulations of the local electromagnetic fields by discrete dipole approximation (DDA) method in the DDSCAT program support the results. 2-nm grids were used for all simulations. The average and maximum electric field intensities over the nanoparticle surface were calculated for isolate metamolecules in a homogenous dielectric environment where the substrate effect was included explicitly by effective media theory. The data was used to produce contour plots of the intensity on and around the nanoparticle to visualize the location of the hotspots. The extinction efficiency was simulated for multiple wavelengths to produce resonance profile and to determine the resonance modes of the metamolecules. The dipole-current diagram of every resonance mode also was produced from the simulation.

When the space between metamolecules is very close, the coupling of electric-magnetic fields between neighboring metamolecules cannot be ignored anymore and the suitable periodical boundary conditions (PBC) must be considered during the simulation. In order to examine how extinction spectra depend on the PBC of choice, the H shape metamaterials of w=30 nm was used with the smallest space as an example to test it. The simulated results of two $P_x$ and $P_y$ polarization configurations are shown in FIG. 10. For the $P_x$ polarization, both of the mode number and spectral shape are almost identical to each other, and the resonant peaks are relatively shifted for different PBC of choice. For the $P_y$ polarization, except the peak shift similar as $P_x$ polarization condition, the spectra widths and profiles show a much stronger PBC dependence than the $P_x$ case. As the increasing of PBC dimension from single metamolecule to 3×3 arrays, the width of spectra, especially the low-energy modes, is broadening. The two dimensional PBC simulation shows a multi-mode profile of low-energy mode. This multi-mode profile is caused by the anisotropy of x-direction PBC and y-direction PBC due to the antisymmetry of the H shape. When PBC increases to the 3×3 arrays, this anisotropy reduces and spectrum shows a broad single peak. Qualitatively, the single metamolecule approximation can give a very good simulation for the real resonance spectra of alphabetical metamaterials with a bar-width of w≥30 nm. Therefore, in the DDA simulations, it took a single metamolecule, unit to produce the data of hot-spot contour plot in FIG. 3 and resonance mode identifications in FIG. 11. In order to give more quantitative results, the 2D PBC was used to produce the resonant profile of SERS signal in FIGS. 2e and 2f.

Besides the analysis based on plasmon hybridization or dipole-dipole coupling theory, DDA simulation was also used to reconfirm the resonant profile and resonant mode identification for all alphabetical metamolecules as shown in FIG. 11. The dipole-current distributions corresponds the FIG. 1c in the main text part. The SEM image of metamaterials was imported as the simulated structure in order to obtain more accurate results. It was found that the simulation by using 60 nm thicknesses was better agreed with the experimental data than the simulation using 30 nm. The physical mechanism is the deference of effective permittivity between evaporated gold film in the resonator and crystalline gold film in simulation. In evaporated gold film in experimental metamaterials, the electron should be experienced more scattering than in crystalline gold, as a results the experimental resonance modes will blue shift comparing the simulated results. In the simulation, the permittivity value of crystalline gold film was used to simulate the evaporated non-crystalline gold film. Consequently, the thicker the gold film simulated, the permitivity was much closer to the value of the crystalline gold film and thus the results strongly agreed with the experimental data. If the accuracy is defined as $$\frac{|\lambda_{exp} - \lambda_{sim}|}{\lambda_{exp} + \lambda_{sim}},$$

the deviation is found to be within 10%.

Enhancement Factor Calculation in DDA Simulation and Experimental Estimation

According to the Mie scattering theory, the electromagnetic enhancement factor (EF) is the production of incident light and scattering light enhancement, i.e.

$$EF_{EM} = \frac{|E(\lambda_{laser})|^2 \times |E(\lambda_{scatt})|^2}{|E_0(\lambda_{laser})|^2 \times |E_0(\lambda_{scatt})|^2},$$

where the $|E(\lambda_{laser})|^2$ and $|E(\lambda_{scatt})|^2$ (or $|E_0(\lambda_{laser})|^2$ and $|E_0(\lambda_{scatt})|^2$) correspond the intensity of localized (or normal) electromagnetic field at incident laser and scattering light wavelength, respectively. During enhancement calculation, usually both of the $|E_0(\lambda_{laser})|^2$ and $|E_0(\lambda_{scatt})|^2$ were normalized to unity. Hence, the enhancement factor can be written as $EF_{EM}=|E(\lambda_{laser})|^2 \times |E(\lambda_{scatt})|^2$. Because the dispersion relation of $|E(\lambda_{laser})|^2$ is proportional to the extinction spectra, the calculated extinction spectra was used to calculate the SERS enhancement depending on the excitation wavelength in FIGS. 2e and 2f. Considering that the scattering wavelength $\lambda_{scatt}$ is very close to the excitation wavelength $\lambda_{laser}$ in Raman spectroscopy, the enhancement factor can be further simplified as zero Stokes shift production of $EF_{EM}=|E(\lambda_{laser})|^4$. This formula was used to calculate the hot-spot distribution and enhancement factor in FIGS. 3b and 3c.

In practical experiments, the enhancement factor (EF) of SERS spectra is defined as follows:

$$EF = \frac{I_{sers}/N_{sers}}{I_{norm}/N_{norm}},$$ (S-1)

where the $I_{sers}$ and $I_{norm}$ are the integral intensities of SERS spectra and normal Raman spectra, respectively. The $N_{sers}$ and $N_{norm}$ are the numbers of molecules contributed to the SERS signal and normal Raman signal, respectively.

For the normal Raman spectra (no SERS-active substrate), 2-Napthalenthiol (2-NAT) powder sample was used as a reference. The number of molecules contributed to normal Raman spectra can be calculated from the equation as follows:

$$N_{norm} = \pi r_{spot}^2 h \times \rho_{2-NAT} \times N_A / M_{2-NAT},$$ (S-2)

where the $\pi r_{spot}^2$ is the area of laser spot at the sample, h is the laser penetration depth in 2-NAT powder sample, which equal to the thickness of 2-NAT powder (h=1 mm) due to total transparent of 2-NAT for 785 nm laser[7], $\rho_{2-NAT}$=1.176 g/cm$^3$ is the density of 2-NAT powder, $N_A$ is the Avogadro constant, and $M_{2-NAT}$=160.24 g/mol is the molecular weight of 2-NAT powder. By substituting those values into the equation (S-2), the new expression of molecule number involving in the SERS signal are as follows:

$$N_{norm} = 4.42 \text{ nm}^{-3} \times \pi r_{spot}^2 h$$ (S-3)

For the SERS spectra of monolayer 2-NAT covered on alphabetical metamaterials, the molecule number contributing to the SERS signal can be calculated by the following equation:

$$N_{SERS} = \frac{(\pi r_{spot}^2 \Box R_{lattice}) \frac{S_{hot-spot}}{S_{lattice}}}{S_{2-NAT}},$$ (S-4)

where the fill factor $R_{lattice}$ is a ratio of the surface area of gold metamaterials to the area of whole unit cell, $S_{hot-spot}$ is the hot-spot area, $S_{lattice}$ is the gold metamaterials area, and $S_{2-NAT}$=0.42 nm$^2$ is the area of single 2-NAT molecule, which is also called molecule boot-print. If the ratio of hot-spot area to gold metamaterials area is defined as $$R_{hot-spot} = \frac{S_{hot-spot}}{S_{lattice}}$$

and combine the equation (S-1), (S-3) and (S-4), the EF can be written as follows:

$$EF = 1.856 \text{ nm}^{-1} h \frac{1}{R_{lattice} R_{hot-spots}} \frac{I_{sers}}{I_{norm}}.$$ (S-5)

Figure 9:
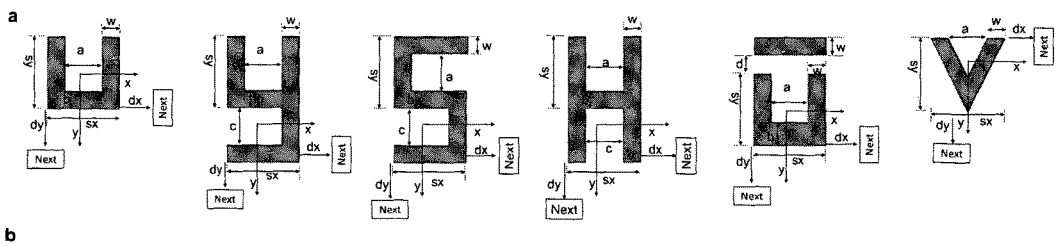
FIG. 9. Geometry definition of alphabetical metamaterials. a, the layout definition of the different alphabet metamaterials with bar width of w=80 nm. b, the actual value of every parameter as labeled in a. The whole size and periodicity of the unit cell are shrunk accordingly from w=80 nm to w=30 nm in order to tune the resonance peak in Vis-NIR range.

For a given pattern with certain size, the $R_{lattice}$ can be easily calculated from the pattern definition as shown in FIG. 9. As an average evaluation, it was supposed that the hot-spot area is equal to the gold pattern area, i.e. $R_{hot-spots}=1$, which is an upper limit of $R_{hot-spots}$ because the hot-spot area is always less than the gold pattern area as shown in FIG. 3c.

Figures 12, 13:
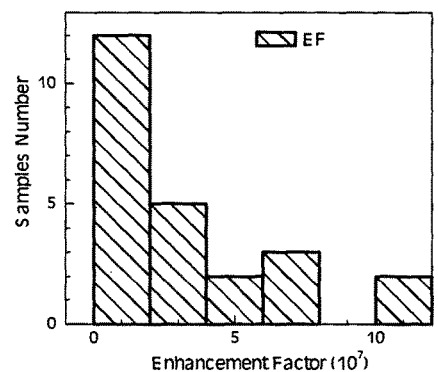
FIG. 12. The enhancement factor calculated for different structures at 785 nm excitation. The normal Raman spectra were measured from a 2-NAT powder with thickness of 1 mm. The $R_{hot\text{-}spots}=1$ was taken as an average enhancement evaluation.
FIG. 13. The histogram plot of SERS enhancement factors.

In order to check the enhancement factor of the alphabet metamaterials, the SERS spectra of monolayer 2-NAT molecules were measured on the metamaterials and power 2-NAT with 1 mm thickness with the same experimental conditions. The results are shown in the FIG. 12. In order to show the statistical results of enhancement factors for different patterns, the measured enhancement factors versus numbers of samples was plotted as shown in FIG. 13. It was found that most of the samples contribute to an EF of ~10$^7$, albeit even there are two samples contributing to an EF ~10$^8$.

The GT-rich oligonucleotide DNA (5'-GGT GGT GGT GGT TGT GGT GGT GGT GG-3') (SEQ ID NO:) was purchased from Integrated DNA Technologies, Singapore. HEPES buffer (50 mM HEPES buffer pH 7.4, 0.1% Triton X-100, 2% dimethyl sulfoxide), Hg(ClO$_4$)$_2$.H$_2$O, and other essential chemicals were of analytical grade and obtained from Sigma-Aldrich, Singapore unless otherwise stated. All experiments were done using DNA-free water (1$^{st}$ Base, Singapore).

We claim:

1. A logic gate, comprising a metamaterial surface enhanced Raman scattering (MetaSERS) sensor, comprising
(a) alphabetical metamaterials in the form of split ring resonators operating in the wavelength range of from 560 nm to 2200 nm; wherein each split ring resonator has a bar width ranging from about 30 nm to about 80 nm; and
(b) a guanine (G) and thymine (T)-rich oligonucleotide that can, upon presence of potassium cations ($K^+$), fold into a G-quadruplex structure, and in presence of $Hg^{2+}$, form a T-$Hg^{2+}$-T hairpin complex that inhibits or disrupts the G-quadruplex structure formed in presence of $K^+$; wherein the concentration of $Hg^{2+}$ ranges from about $2\times10^{-4}$ ppb to about $4\times10^{-1}$ ppb to form the T-$Hg^{2+}$-T hairpin complex;
wherein the alphabetical metamaterials are configured to generate a SERS signal based on the configuration of the G- and T-rich oligonucleotide to be detected by the MetaSERS sensor.

2. The logic gate according to claim 1, wherein the alphabetic metamaterials are disposed on a substrate to form the split ring resonators.

3. The logic gate according to claim 1, wherein the split ring resonators are U, V, H, S, Ü or Y-shaped and have a bar width from 30 to 50 nm.

4. The logic gate according to claim 1, wherein the split ring resonators comprise a noble metal film deposited on their surface.

5. The logic gate according to claim 4, wherein the noble metal film comprises gold, silver, or alloys thereof.

6. The logic gate according to claim 1, wherein the G- and T-rich oligonucleotide has the consensus nucleotide sequence $(((g)_x(t)_y)_m(X)_n((t)_y(g)_x)_o)_p$, wherein X is a, g, t, or c, each x is independently an integer from 1 to 4, each y is independently 1 or 2, each m is independently an integer from 1 to 10, each n is independently an integer from 1 to 10, each o is independently an integer from 1 to 10, and p is an integer from 1 to 5, wherein m+o= at least 4.

7. The logic gate of claim 1, wherein the oligonucleotide sequence has a length of up to 50 nucleotides.

8. The logic gate of claim 1, wherein the oligonucleotide comprises or consists of the nucleotide sequence $(GGT)_4TG(TGG)_4$ (SEQ ID NO:1).

9. The logic gate of claim 1, wherein the oligonucleotide is single-stranded DNA (ssDNA).

10. A method of operating the logic gate according to claim 1, the method comprising:
(a) providing the MetaSERS sensor, wherein the oligonucleotide is comprised in an aqueous solution, wherein the split ring resonators are immersed in the aqueous solution;
(b) adding one or more ions selected from the group consisting of potassium ions ($K^+$), mercury ions ($Hg^{2+}$), iodide ions ($I^-$), and combinations thereof; wherein the one or more ions are added at the same time or different times and in any order to generate an AND, OR or INHIBIT logic operation; and
(c) measuring a SERS signal based on a structure formed by the oligonucleotide after adding the one or more ions.

11. The logic gate of claim 1, wherein the logic gate further comprises one or both of potassium ions and $Hg^{2+}$ to allow two or more logic gate operations selected from the group consisting of "AND," "OR," "INHIBIT," and combinations thereof.

12. The logic gate of claim 1, wherein the concentration of $Hg^{2+}$ ranges from about $2\times10^{-4}$ ppb to about $4\times10^{-2}$ ppb to form the T-$Hg^{2+}$-T hairpin complex.

13. The logic gate of claim 1, wherein the concentration of $Hg^{2+}$ ranges from about $2\times10^{-4}$ ppb to about $4\times10^{-3}$ ppb to form the T-$Hg^{2+}$-T hairpin complex.

14. A method for the detection of mercury ions ($Hg^{2+}$) in a sample, the method comprising:
(a) providing a MetaSERS sensor, comprising alphabetical metamaterials in the form of split ring resonators operating in the wavelength range of from 560 nm to 2200 nm; wherein each split ring resonator has a bar width ranging from about 30 nm to about 80 nm; and an aqueous solution comprising a guanine (G) and thymine (T)-rich oligonucleotide, wherein in the presence of the potassium cations ($K^+$) the oligonucleotide adopts a G-quadruplex structure, and in presence of $Hg^{2+}$, forms a T-$Hg^{2+}$-T hairpin complex that inhibits or disrupts the G-quadruplex structure, wherein the aqueous solution is in contact with the split ring resonators; wherein the concentration of fig' ranges from about $2\times10^4$ ppb to about $4\times10^{-1}$ ppb to form the T-$Hg^{2+}$-T hairpin complex;
(b) contacting the MetaSERS sensor with the sample in the presence of potassium ions ($K^+$) under conditions that allow any $Hg^{2+}$ that is present in the sample to form a T-$Hg^{2+}$-T hairpin complex with the oligonucleotide that inhibits formation of or disrupts the G-quadruplex structure; and
(c) measuring a SERS signal based on a structure formed by the oligonucleotide after adding $K^+$.

15. The method of claim 14 wherein the sample is an environmental sample, a food sample or a biological sample.

* * * * *

UNITED STATES PATENT AND TRADEMARK OFFICE
CERTIFICATE OF CORRECTION

PATENT NO.       : 10,466,180 B2
APPLICATION NO.  : 14/896515
DATED            : November 5, 2019
INVENTOR(S)      : Xiong et al.

Page 1 of 1

It is certified that error appears in the above-identified patent and that said Letters Patent is hereby corrected as shown below:

Column 24, Claim 14, Line 53:
"resonators; wherein the concentration of fig' ranges from" should read, --resonators; wherein the concentration of $Hg^{2+}$ ranges from--

Column 24, Claim 14, Line 54:
"about $2\times10^4$ ppb to about $4\times10^{-1}$ ppb to form the" should read, --about $2\times10^{-4}$ ppb to about $4\times10^{-1}$ ppb to form the--

Signed and Sealed this
Eighth Day of September, 2020

Andrei Iancu
*Director of the United States Patent and Trademark Office*